US012575785B2

(12) United States Patent　　　　　(10) Patent No.: US 12,575,785 B2
Seo et al.　　　　　　　　　　　　　　(45) Date of Patent: Mar. 17, 2026

(54) METHOD, APPARATUS AND COMPUTER PROGRAM FOR READING ROTATOR CUFF TEAR STATE OR MUSCLE FAT DEGENERATION DISORDER BASED ON ARTIFICIAL INTELLIGENCE

(71) Applicant: SeeAnn Solution Co., Ltd., Incheon (KR)

(72) Inventors: Anna Seo, Incheon (KR); Youngjin Jeong, Incheon (KR); Seokwon Chung, Seoul (KR)

(73) Assignee: SeeAnn Solution Co., Ltd., Incheon (KR)

( * ) Notice: Subject to any disclaimer, the term of this patent is extended or adjusted under 35 U.S.C. 154(b) by 478 days.

(21) Appl. No.: 18/114,139

(22) Filed: Feb. 24, 2023

(65) Prior Publication Data

US 2023/0293094 A1　　Sep. 21, 2023

(30) Foreign Application Priority Data

Feb. 25, 2022　(KR) ........................ 10-2022-0025202
Feb. 25, 2022　(KR) ........................ 10-2022-0025203

(51) Int. Cl.
　　*A61B 5/00*　　　　(2006.01)
　　*G06T 7/10*　　　　(2017.01)
　　*G06V 10/25*　　　(2022.01)
(52) U.S. Cl.
　　CPC .............. *A61B 5/4576* (2013.01); *G06T 7/10* (2017.01); *G06V 10/25* (2022.01); *G06T 2207/20084* (2013.01)

(58) Field of Classification Search
　　CPC ................... A61B 5/4576; G06T 7/10; G06T 2207/20084; G06V 10/25
　　USPC ...................................................... 600/587
　　See application file for complete search history.

(56) References Cited

U.S. PATENT DOCUMENTS

| | | | |
|---|---|---|---|
| 2020/0167911 A1* | 5/2020 | Park ......................... | G06T 7/11 |
| 2020/0237452 A1* | 7/2020 | Wolf ....................... | G06F 3/048 |
| 2022/0039868 A1* | 2/2022 | Chaoui .................. | A61B 34/25 |

FOREIGN PATENT DOCUMENTS

| | | |
|---|---|---|
| KR | 10-2021-0007260 A | 1/2021 |
| KR | 10-2291854 B | 8/2021 |
| KR | 10-2021-0124559 A | 10/2021 |

OTHER PUBLICATIONS

Shin (Shin, Keun Man. "Partial-Thickness Rotator Cuff Tears." The Korean Journal of Pain 24 (2011): 69-73; downloaded from https://api.semanticscholar.org/CorpusID:7469082 on Jul. 22, 2025) (Year: 2011).*

(Continued)

*Primary Examiner* — Mark Edwards
(74) *Attorney, Agent, or Firm* — Studebaker Brackett PLLC

(57)　　　　　　　　ABSTRACT

Provided is a method performed by an apparatus for reading a shoulder disorder, the method including acquiring medical data including a shoulder image; preprocessing the acquired medical data; inputting the preprocessed medical data into a pre-trained neural network model to read a tear state of a rotator cuff; and generating result information on the medical data based on the read tear state of the rotator cuff.

13 Claims, 12 Drawing Sheets
(8 of 12 Drawing Sheet(s) Filed in Color)

(56) References Cited

OTHER PUBLICATIONS

Novi et al. (Novi M, et al. Irreparable rotator cuff tears: challenges and solutions. Orthop Res Rev. Dec. 5, 2018;10:93-103. doi: 10.2147/ORR.S151259; downloaded from https://www.dovepress.com/irreparable-rotator-cuff-tears-challenges-and-solutions-peer-reviewed-fulltext-article-ORR on Jul. 22, 2025) (Year: 2018).*

An Office Action mailed by the Korean Intellectual Property Office on Apr. 25, 2024, which corresponds to Korean Patent Application No. 10-2022-0025202 and is related to U.S. Appl. No. 18/114,139.

Sinhye Song et al.; "Partial-Thickness Tear of Supraspinatus and Infraspinatus Tendon Revisited: Based on MR Findings"; Journal of The Korean Society of Radiology; 2021 (Nov. 30, 2021); pp. 1366-1387; with partial English language translation.

"Method of calculating the cost of shoulder plastic surgery and rotator cuff tear restoration"; Blog, https://blog.naver.com/suriowl7/222013010396; Jun. 26, 2020; total 3 pages.

An Office Action mailed by the Korean Intellectual Property Office on Apr. 25, 2024, which corresponds to Korean Patent Application No. 10-2022-0025203 and is related to U.S. Appl. No. 18/114,139.

Kyunghan Ro et al.; "Deep-learning framework and computer assisted fatty infiltration analysis for the supraspinatus muscle in MRI"; Scientific Reports; 2021 (Jul. 23, 2021); total 12 pages.

Joong-Bae Seo et al.; "Relationship of the Sagittal Extent of Rotator Cuff Tears to the Grade of Fatty Degeneration of the Rotator Cuff Muscles"; Clinics in Shoulder and Elbow; Dec. 2011; pp. 159-164; vol. 14, No. 2; with partial English language translation.

* cited by examiner

| Grade 0 | Grade 1 | Grade 2 | Grade 3 | Grade 4 |
|---------|---------|---------|---------|---------|
| Normal | Some fat streaks | Less fat than muscle | As much fat as muscle | More fat than muscle |

METHOD, APPARATUS AND COMPUTER PROGRAM FOR READING ROTATOR CUFF TEAR STATE OR MUSCLE FAT DEGENERATION DISORDER BASED ON ARTIFICIAL INTELLIGENCE

CROSS-REFERENCE TO RELATED APPLICATION

This application is based on and claims the benefit of priority to Korean Patent Application No. 10-2022-0025202, filed on Feb. 25, 2022, and Korean Patent Application No. 10-2022-0025203, filed on Feb. 25, 2022, the disclosures of which are incorporated herein in their entirety by reference.

BACKGROUND

1. Field of the Invention

The present invention relates to a method of reading a shoulder disorder, and more specifically, to a method, apparatus, and computer program apparatus that are capable of reading a rotator cuff tear state or a rotator cuff muscle fat degeneration among shoulder disorders from medical data.

2. Discussion of Related Art

Generally, medical images provide significant assistance to medical practitioners in patent diagnosis by allowing the inside of a patient's body to be checked.

For example, whether there are abnormalities in the shoulder, heart, lungs, bronchus, and the like may be checked through medical images.

However, in some medical images, the reading difficulty is so high that even medical practitioners with many years of experience have a difficulty in making a rapid diagnose.

In particular, in the case of medical images, with regard to rotator cuff tendinitis or tear among shoulder disorders, it is difficult for a medical practitioner to visually accurately read the degree of a tear through a medical image.

In recent years, neural network models capable of performing direct reading from input images are being used, but such a method may cause an overfitting when data is insufficient or improperly collected, and it is impossible to identify which part has been used by the neural network model in making a diagnosis, and thus utilization of neural network models may be lowered.

Therefore, a method of reading a shoulder disorder using a neural network model to assist medical practitioners with diagnosing shoulder disorders is needed. This results was supported by "Regional Inovation Strategy (RIS)" through the National Research Foundation of Korea (NRF) funded by the Ministry of Education (MOE). (2021RIS-001 (1345341783)).

RELATED ART DOCUMENTS

Patent Document (PATENT DOCUMENT 1) Korean Registered Patent No. 10-2291854 (Aug. 13, 2021)

SUMMARY OF THE INVENTION

The present invention is directed to providing a method, apparatus, and computer program apparatus that are capable of increasing the accuracy in reading a rotator cuff tear by preprocessing medical data to segment a target region for reading a rotator cuff tear, and inputting the target region into a pre-trained neural network model to read a tear state of a rotator cuff.

The present invention is directed to providing a method, apparatus, and computer program apparatus that are capable of increasing the accuracy in reading a fat degeneration of a rotator cuff by preprocessing medical data to segment a target region for reading a fat degeneration of the rotator cuff, and inputting the target region into a pre-trained neural network model to read a fat degeneration state of a rotator cuff.

The technical objectives of the present invention are not limited to the above, and other objectives may become apparent to those of ordinary skill in the art based on the following descriptions.

According to an aspect of the present invention, there is provided a method of reading a shoulder disorder, the method including: acquiring medical data including a shoulder image; preprocessing the acquired medical data; inputting the preprocessed medical data into a pre-trained neural network model to read a tear state of a rotator cuff; and generating result information on the medical data based on the read tear state of the rotator cuff.

The preprocessing of the acquired medical data may include segmenting a target region for reading a rotator cuff tear from the acquired medical data.

The preprocessing of the acquired medical data may include: when segmenting the target region for reading the rotator cuff tear, segmenting a rotator cuff region using a pre-learned segmentation model; and designating a region affecting classification as a region of interest (ROI).

The pre-trained segmentation model may be a two-dimensional (2D) segmentation model including a 2D U-Net or a three-dimensional (3D) segmentation model including a 3D U-Net.

The designated ROI may include a location point of muscles and tendons surrounding a glenoid located between a scapula and a humerus.

The reading of the tear state of the rotator cuff may include, through the pre-trained neural network model: firstly reading whether the tear state of the rotator cuff is a normal state or an abnormal state; and when a result of the reading is that the tear state of the rotator cuff is an abnormal state, secondly reading whether the rotator cuff is in a partial tear state or a full-thickness tear state.

The reading of whether the rotator cuff is in the partial tear state may include reading whether the rotator cuff is in a partial tear state with a tear less than 50% or the rotator cuff is in a partial tear state with a tear greater than or equal to 50%.

The reading of whether the rotator cuff is in the partial tear state may include: when the rotator cuff is in a partial tear state with a tear less than 50%, reading that a surgery may not be required; and when the rotator cuff is in a partial tear state with a tear greater than or equal to 50%, reading that a surgery may be required.

The reading of whether the rotator cuff is in the full-thickness tear state may include reading whether the rotator cuff is in a full-thickness tear state with a one-tendon tear, whether the rotator cuff is in a full-thickness tear state with a two-tendon tear, or whether the rotator cuff is in a full-thickness tear state with a three-tendon tear.

The reading of whether the rotator cuff is in the full-thickness tear state may include: when a result of the reading is that the rotator cuff is in a full-thickness tear state with a one-tendon tear, reading a first insurance fee code corresponding to the result; when a result of the reading is that the rotator cuff is in a full-thickness tear state with a two-tendon tear, reading a second insurance fee code corresponding to the result; and when a result of the reading is that the rotator cuff is in a full-thickness tear state with a three-tendon tear, reading a third insurance fee code corresponding to the result.

The reading of whether the rotator cuff is in the full-thickness tear state may include reading whether the rotator cuff is in a full-thickness tear state with a tendon tear less than 2.5 cm, whether the rotator cuff is in a full-thickness tear state with a tendon tear greater than or equal to 2.5 cm, or whether the rotator cuff is in a full-thickness tear state with a tendon tear greater than or equal to 2.5 cm, or a subscapularis tear requiring suturing.

The reading of whether the rotator cuff is in the full-thickness tear state may include, when a result of the reading is that the rotator cuff is in a full-thickness tear state with a tendon tear less than 2.5 cm, reading a first insurance fee code corresponding to the result, and when a result of the reading is that the rotator cuff is in a full-thickness tear state with a tendon tear greater than or equal to 2.5 cm, reading a second insurance fee code corresponding to the result, and when a result of the reading is that the rotator cuff is in a full-thickness tear state with a tendon tear greater than or equal to 2.5 cm or a subscapularis tear requiring, reading a third insurance fee code corresponding to the result.

The generating of result information on the medical data may include generating result information for visualizing the result of reading the tear state of the rotator cuff based on the read tear state of the read rotator.

According to an aspect of the present invention, there is provided a computer program stored on a computer readable recording medium, the computer program that, when executed by one or more processors, performs following operations for reading a shoulder disorder, the operations including: an operation of acquiring medical data including a shoulder image; an operation of preprocessing the acquired medical data; an operation of inputting the preprocessed medical data into a pre-trained neural network model to read a tear state of a rotator cuff; and an operation of generating result information on the medical data based on the read tear state of the rotator cuff.

According to an aspect of the present invention, there is provided a computing device for providing a method of reading a shoulder disorder, the computing device including: a processor including one or more cores; and a memory, wherein the processor is configured to: acquire medical data including a shoulder image; preprocess the acquired medical data; input the preprocessed medical data into a pre-trained neural network model to read a tear state of a rotator cuff; and generate result information on the medical data based on the read tear state of the rotator cuff.

A computer program for providing a method of reading a shoulder disorder according to another aspect of the present invention is stored in a medium so as to be executed in combination with a computer, which is hardware.

In addition, other methods and other systems for implementing the present invention, and a computer readable recoding medium that records a computer program for executing the method may be further provided.

According to an aspect of the present invention, there is provided a method of reading a shoulder disorder, the method including: acquiring medical data including a shoulder image; preprocessing the acquired medical data; inputting the preprocessed medical data into a pre-trained neural network model to read a fat degeneration of a rotator cuff;

and generating result information on the medical data based on the read fat degeneration state of the rotator cuff.

The preprocessing of the acquired medical data may include segmenting a target region for reading the fat degeneration of the rotator cuff based on a shading change of the medical data.

The preprocessing of the acquired medical data may include: calculating a shading change rate from the medical data; detecting a region in which the calculated shading change rate is greater than or equal to a reference value as a target region for reading a fat degeneration of the rotator cuff; and segmenting the detected target region.

The target region for reading the fat degeneration of the rotator cuff may include a supraspinatus (SS) region, an infraspinatus (IS) region, a teres minor (TM) region, and a subscapularis (Su) region.

The reading of the fat degeneration state of the rotator cuff may include, through the pre-trained neural network model: firstly reading whether a fat degeneration state of the rotator cuff is a normal state or an abnormal state; and when a result of the reading is that the fat degeneration state of the rotator cuff is an abnormal state, secondly reading a fat degeneration level of the rotator cuff.

The reading of the fat degeneration level of the rotator cuff may include calculating a degree of fat degeneration based on an area of fat present in the rotator cuff, and reading the fat degeneration level based on the calculated degree of fat degeneration.

The degree of fat degeneration may be calculated based on a formula expressed as $(B-A)/B$, wherein B may be an area of the rotator cuff, and A may be an area excluding fat occupying the rotator cuff.

The degree of fat degeneration of the supraspinatus may be calculated based on a formula expressed as $(B-A)/B$, wherein B may be the total area of a supraspinatus region, and A may be an area excluding fat occupying the supraspinatus region.

The degree of fat degeneration of the infraspinatus may be calculated based on a formula expressed as $(B-A)/B$, wherein B may be the total area of a infraspinatus region, and A may be an area excluding fat occupying the infraspinatus region.

The degree of fat degeneration of the teres minor may be calculated based on a formula expressed as $(B-A)/B$, wherein B may be the total area of a teres minor region, and A may be an area excluding fat occupying the teres minor region.

The degree of fat degeneration of the subscapularis may be calculated based on a formula expressed as $(B-A)/B$, wherein B may be the total area of a subscapularis region, and A may be an area excluding fat occupying the subscapularis region.

The neural network model may be pre-trained to, in response that the target region for reading a fat degeneration of the rotator cuff, which is segmented from the medical data, is input thereto, read a fat degeneration state of the rotator cuff.

The neural network model may be pre-trained to, in response that the target region for reading a fat degeneration of the rotator cuff, which is segmented from the medical data, is input thereto, read a fat degeneration state of the rotator cuff, and calculate the degree of fat degeneration based on a result of reading the fat degeneration state of the rotator cuff to read a fat degeneration level.

The generating of the result information on the medical data may include generating result information including a treatment guide based on the read fat degeneration state of the rotator cuff.

According to an aspect of the present invention, there is provided a computer program stored on a computer readably recording medium, the computer program that, when executed by one or more processors, performs following operations for reading a shoulder disorder, the operations including: an operation of acquiring medical data including a shoulder image; an operation of preprocessing the acquired medical data; an operation of inputting the preprocessed medical data into a pre-trained neural network model to read a fat degeneration of a rotator cuff; and an operation of generating result information on the medical data based on the read fat degeneration state of the rotator cuff.

According to an aspect of the present invention, there is provided a computing device for providing a method of reading a shoulder disorder, the computing device including: a processor including one or more cores; and a memory, wherein the processor is configured to: acquire medical data including a shoulder image; pre-process the acquired medical data; input the preprocessed medical data into a pre-trained neural network model to read a fat degeneration of a rotator cuff; and generate result information on the medical data based on the read fat degeneration state of the rotator cuff.

A computer program for providing a method of reading a shoulder disorder according to another aspect of the present invention is stored in a medium so as to be executed in combination with a computer, which is hardware.

In addition, other methods and other systems for implementing the present invention, and a computer readable recoding medium that records a computer program for executing the method may be further provided.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and advantages of the present invention will become more apparent to those of ordinary skill in the art by describing exemplary embodiments thereof in detail with reference to the accompanying drawings, in which.

6

Figure 8:
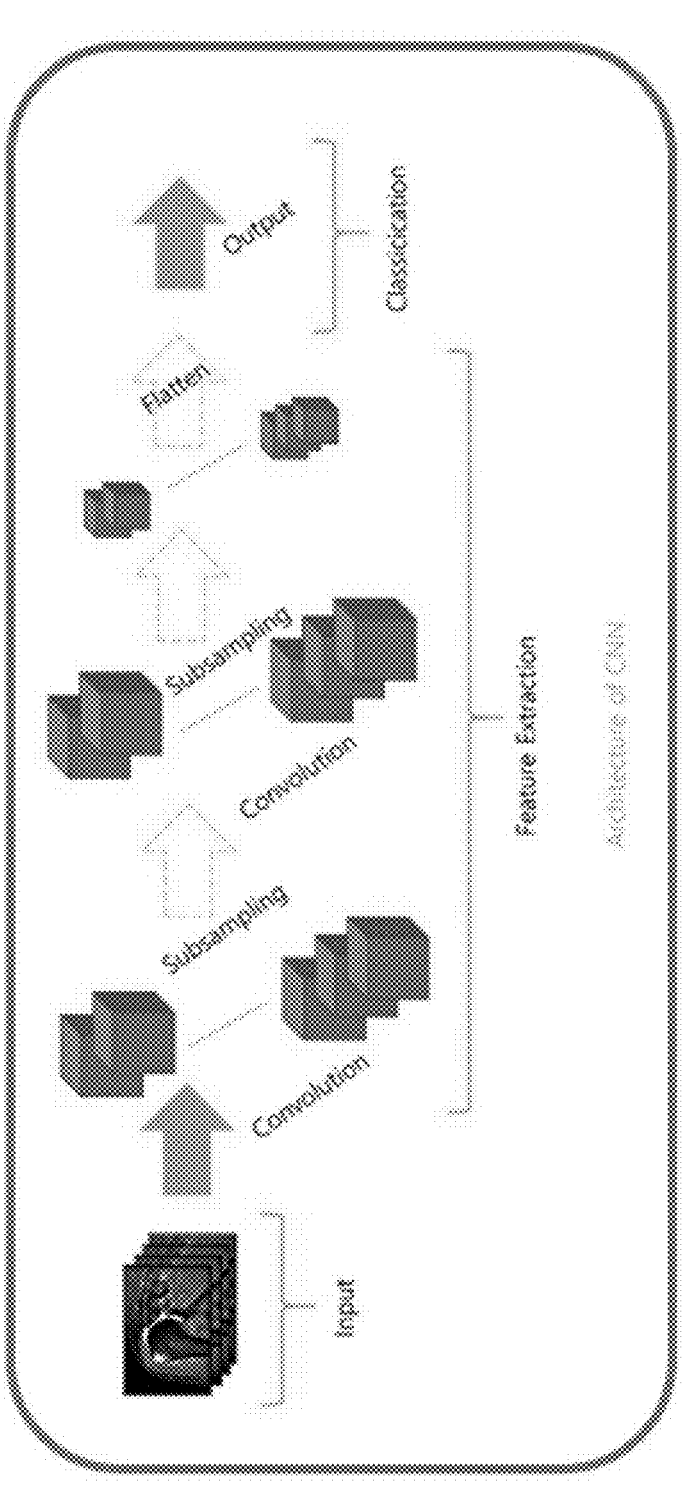
Figure 9:
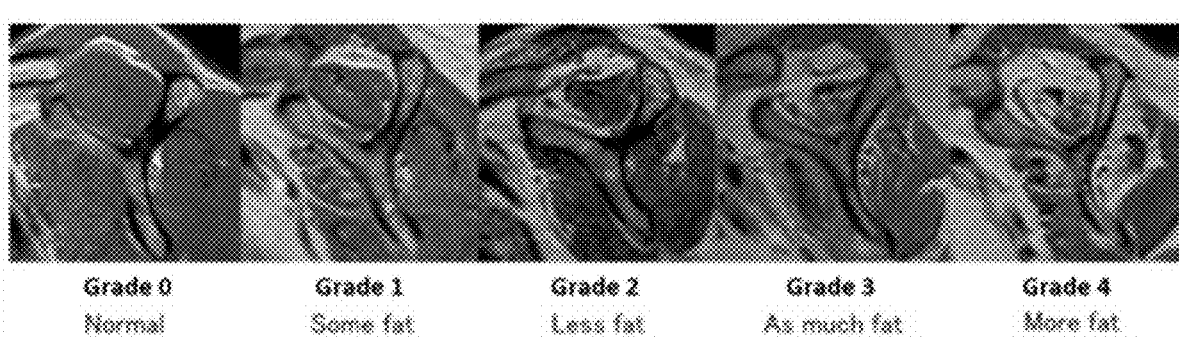
Figure 10:
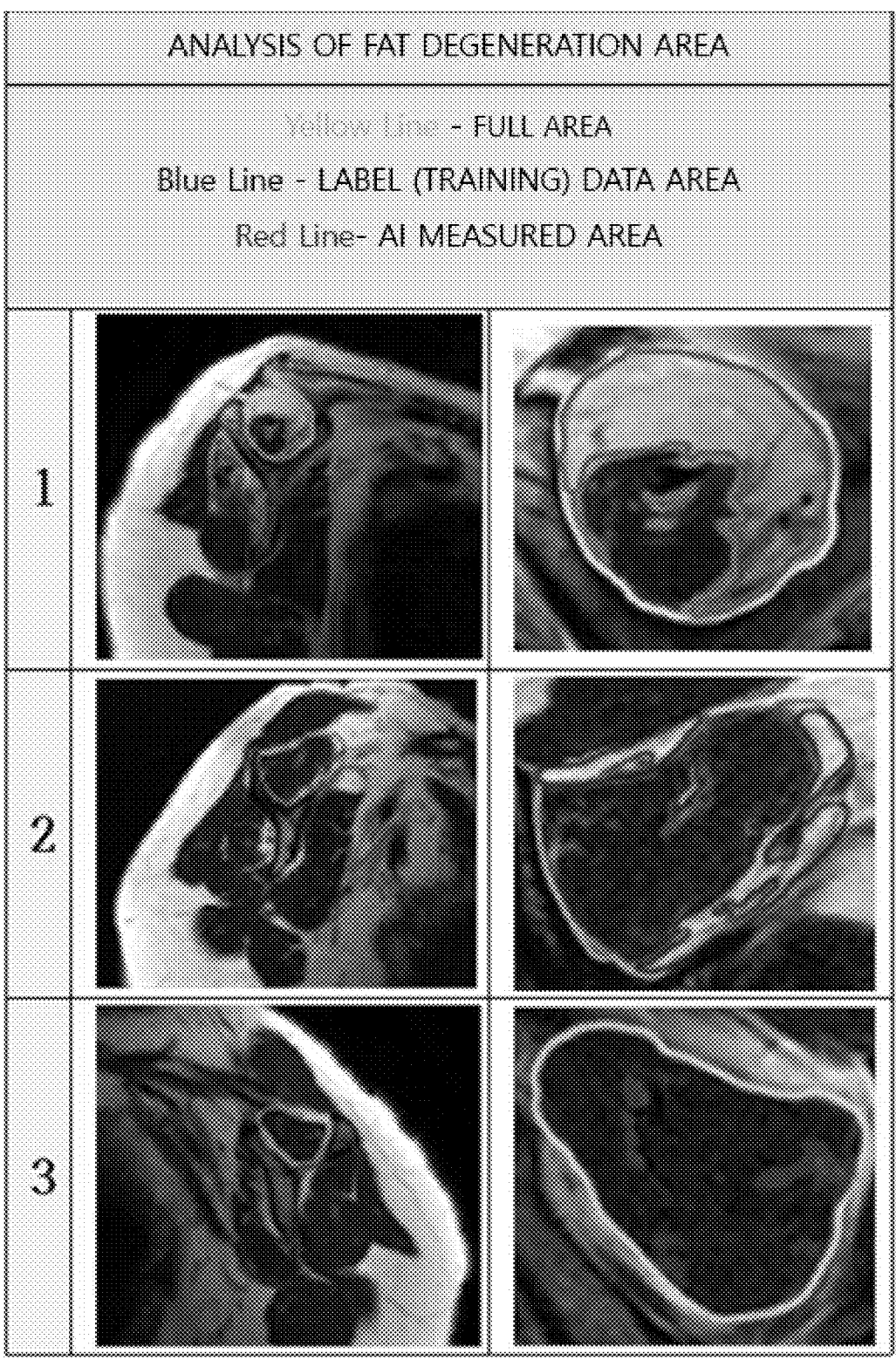
Figure 11:
Figure 12:
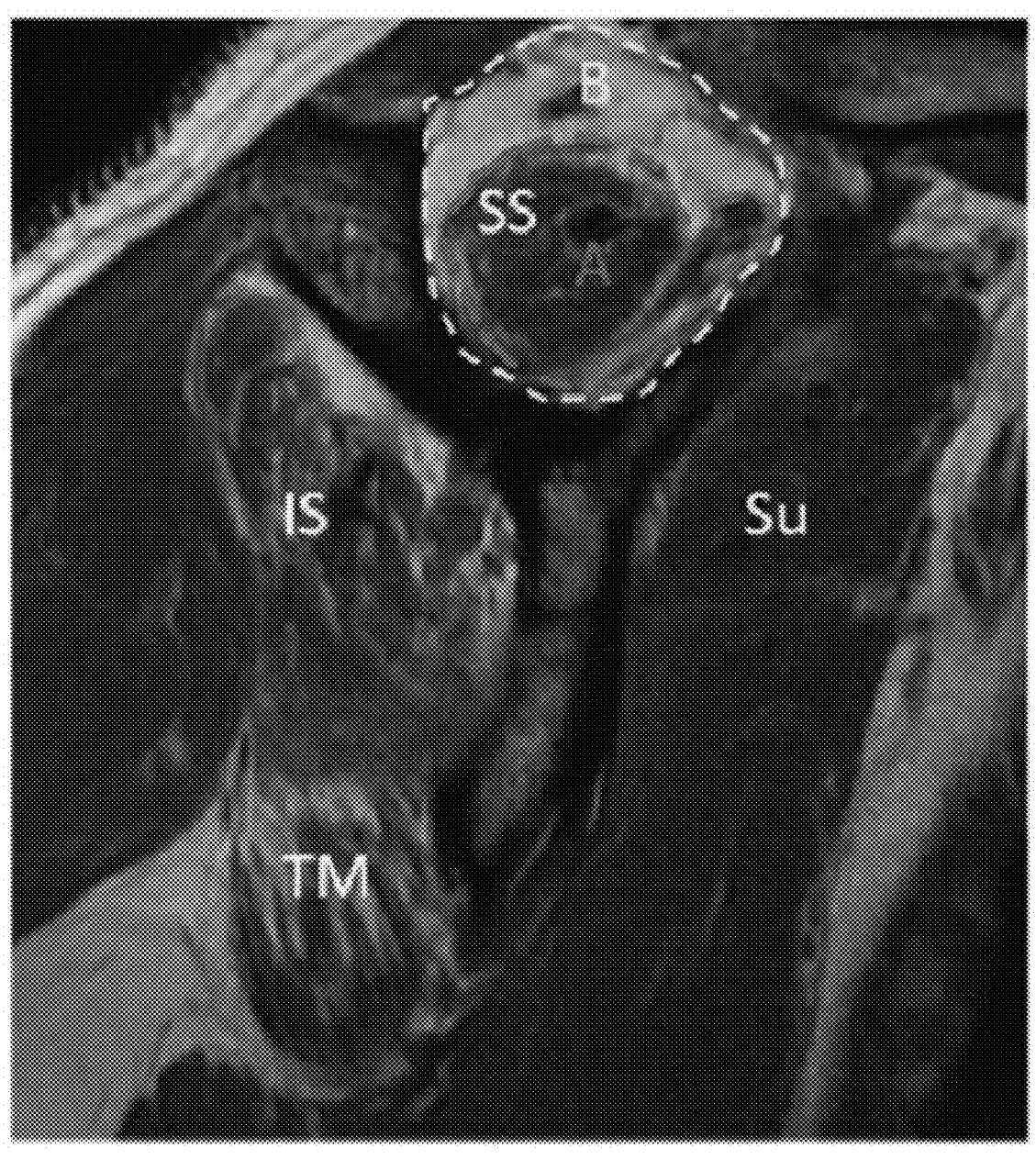
Figure 13:
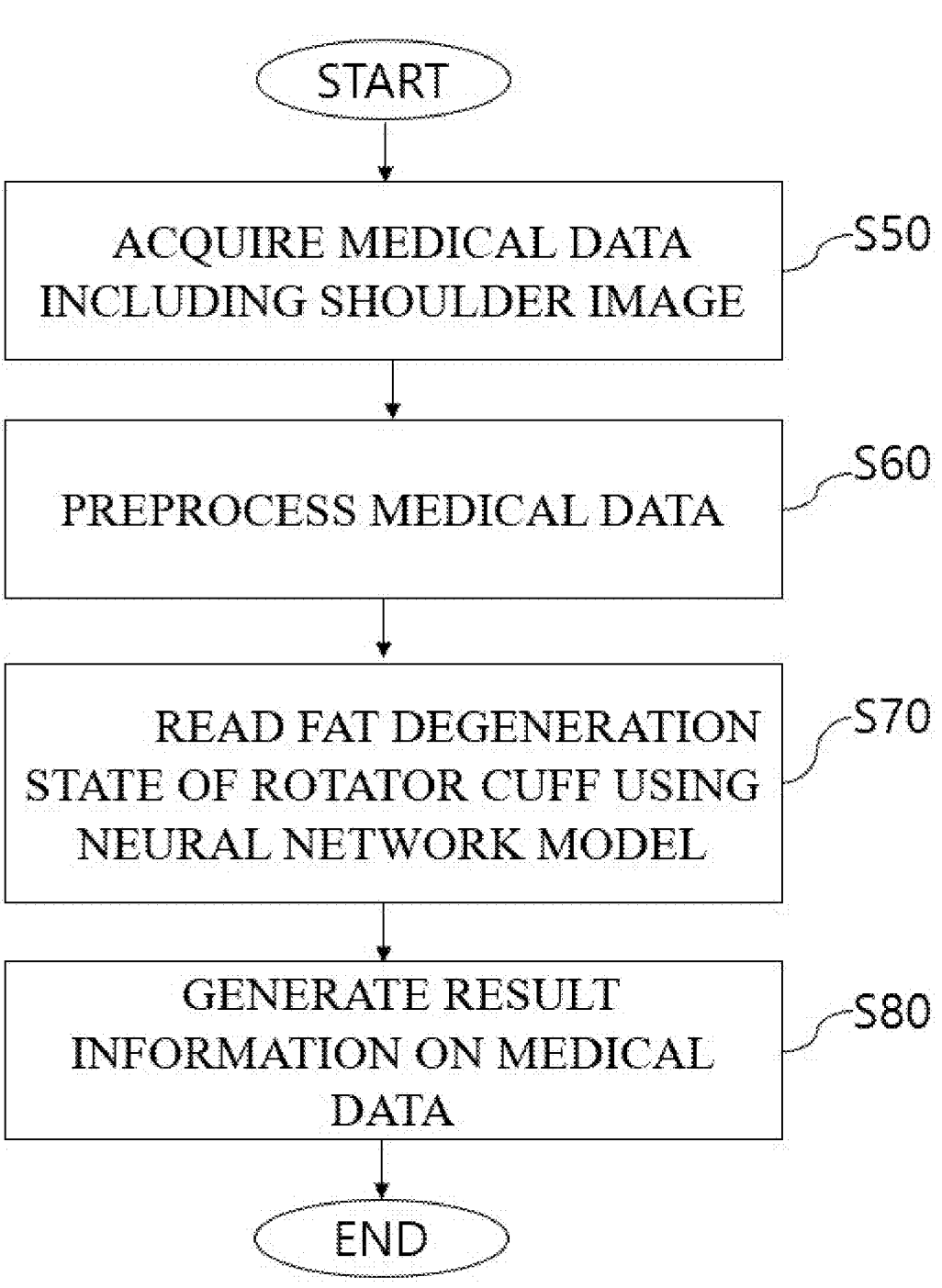

FIG. 8 is a schematic diagram illustrating a network function for reading a shoulder disorder, according to another embodiment of the present invention;

FIG. 9 is a diagram showing segmented images for reading a fat degeneration level of a rotator cuff, according to another embodiment of the present invention;

FIG. 10 is a diagram showing preprocessed images of a fat degeneration area of a rotator cuff, according to another embodiment of the present invention;

FIGS. 11 and 12 are diagrams showing preprocessed images for describing a process of calculating the degree of fat degeneration of a rotator cuff, according to another embodiment of the present invention; and FIG. 13 is a flowchart for describing a method of reading a shoulder disorder, according to another embodiment of the present invention.

DETAILED DESCRIPTION OF EXEMPLARY EMBODIMENTS

Hereinafter, the advantages and features of the present invention and ways of achieving them will become readily apparent with reference to the following embodiments described in detail in conjunction with the accompanying drawings. However, the present invention is not limited to such embodiments and may be embodied in various forms. The embodiments to be described below are provided only to make the disclosure of the present invention complete and assist those of ordinary skill in the art in fully understanding the scope of the present invention, and the scope of the present invention is defined only by the appended claims.

Terms used herein are used for aiding in the description and understanding of the embodiments and are not intended to limit the scope and spirit of the present invention. It should be understood that the singular forms "a" and "an" also include the plural forms unless the context clearly dictates otherwise. The terms "comprises," "comprising," "includes," and/or "including," when used herein, specify the presence of stated features, integers, steps, operations, elements, components and/or groups thereof and do not preclude the presence or addition of one or more other features, integers, steps, operations, elements, components, and/or groups thereof. In connection with assigning reference numerals to elements in the drawings, the same reference numerals are used for designating the same elements throughout the specification, and the term "and/or" includes any one or combinations of the associated listed items. It should be understood that, although the terms "first," "second," etc. may be used herein to describe various elements, these elements are not limited by these terms. These terms are only used for distinguishing one element from another. For example, a first element could be termed a second element without departing from the scope of the present invention.

Unless otherwise defined, all terms (including technical and scientific terms) used herein have the same meaning as commonly understood by one of ordinary skill in the art to which this invention belongs. It should be further understood that terms, such as those defined in commonly used dictionaries, should not be interpreted in an idealized or overly formal sense unless expressly specifically defined herein.

Hereinafter, embodiments of the present invention will be described in detail with reference to the accompanying drawings.

Before describing the embodiments of the present invention, the meaning of terms used in this specification will be briefly described. However, the description of terms is merely intended to aid in the understanding of the present specification rather than limiting the technical spirit of the present invention.

In this specification, neural networks, artificial neural networks, and network functions may often be used interchangeably.

The term "image" or "image data" used throughout the description and claims of the present invention refers to multidimensional data composed of discrete image elements (e.g., pixels in a two dimensional image), in other words, an object that is visible (e.g., displayed on a video screen) or a digital representation thereof (e.g., a file corresponding to a pixel output of a computed tomography (CT) detector, a magnetic resonance imaging (MRI) detector, etc.).

For example, an "image" may be a CT image, a MRI image, a hyoid bone image, an ultrasound image, or other medical images of a subject that are collected by any other medical imaging system known in the art. The image is not necessarily provided in a medical context, but may be provided in a non-medical context, for example X-ray imaging for security screening.

Throughout the detailed description and claims of the present invention, the DICOM (Digital Imaging and Communications in Medicine) standard is a generic term for various standards used for digital image expression and communication in medical devices. The DICOM standard is published by an association committee formed by the American Radiological Society (ACR) and the American Electrical Association (NEMA).

In addition, throughout the detailed description and claims of the present invention, a medical image storage and transmission system (PACS; Picture Archiving and Communication System) is a term that refers to a system that stores, processes, and transmits images according to the DICOM standard, images acquired using digital medical imaging equipment, such as X-ray, CT, and MRI equipment may be stored in a DICOM format and transmitted to terminals inside and outside a hospital through a network, and reading results and medical records may be added to this.

In addition, throughout this specification, a neural network, and a network function may be used with the same meaning. A neural network may be composed of a set of interconnected computational units, which may be generally referred to as "nodes". The "nodes" may also be referred to as "neurons". A neural network includes at least two nodes. Nodes (or neurons) constituting a neural network may be interconnected by one or more "links".

Figure 1:
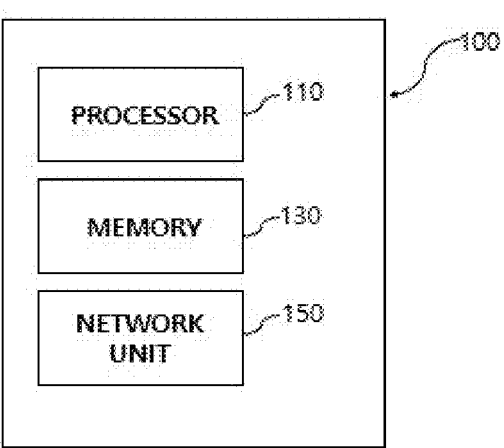
FIG. 1 is a block diagram illustrating a computing device that performs an operation for providing a method of reading a shoulder disorder, according to an embodiment of the present invention.

FIG. 1 is a block diagram illustrating a computing device that performs an operation for providing a method of reading a shoulder disorder, according to an embodiment of the present invention.

The configuration of a computing device 100 shown in FIG. 1 is only a simplified example. In one embodiment of the present invention, the computing device 100 may include other components for performing a computing environment of the computing device 100, and only some of the disclosed components may constitute the computing device 100.

The computing device 100 may include a processor 110, a memory 130, and a network unit 150.

In the present invention, the processor 110 may acquire medical data including a shoulder image, pre-process the acquired medical data, input the preprocessed medical data into a pre-trained neural network model to read a tear state of a rotator cuff (hereinafter, referred to as a rotator cuff tear state), and generate result information on the medical data based on the read rotator cuff tear state.

In addition, in the present invention, the processor 110 may acquire medical data including a shoulder image, preprocess the acquired medical data, input the preprocessed medical data into a pre-trained neural network model to read a fat degeneration of a rotator cuff, and generate result information on the medical data based on the read fat degeneration state of the rotator cuff.

Here, the medical data may include at least one of image data, speech data, or time series data. That is, the medical data may include any type of data by which a person engaged in the medical industry or an apparatus for diagnosis may identify the presence or absence of a disease in data. The image data includes all types of image data of a patient's affected part that is photographed or measured through examination equipment, and then converted into an electrical signal and output. The image data may include image data that, once a video has been consecutively photographed over time by a medical imaging apparatus, constitutes each frame of the video. For example, the image data includes ultrasound examination image data, image data by an MRI apparatus, CT tomography image data, X-ray image data, and the like. Furthermore, when speech data is converted into an electrical signal and output as an image in the form of a graph, or time-series data is expressed as visualized data, such as a graph, the image or data may be included in the image data. For example, medical data may include CT images. The above described examples of medical data are only examples and do not limit the present disclosure.

In one embodiment, the medical data may include a shoulder MRI image, but this is only an embodiment, and the present invention is not limited thereto.

Next, the processor 110 may, when preprocessing the acquired medical data, segment a target region for reading a rotator cuff tear from the acquired medical data.

Here, the processor 110 may, when segmenting the target region for reading a rotator cuff tear, use a pre-trained segmentation model to segment a rotator cuff region and designate a region affecting classification as a region of interest (ROI).

For example, the pre-trained segmentation model may be a two-dimensional (2D) segmentation model including a 2D U-Net or a three-dimensional (3D) segmentation model including a 3D U-Net.

In addition, the designated ROI may include a location point of muscles and tendons surrounding a glenoid located between a scapula and a humerus, which is only one embodiment, and the present invention is not limited thereto.

In some cases, the processor 110 may, when preprocessing the acquired medical data, segment a target region for reading a rotator cuff tear based on a shading change of the medical data.

Here, the processor 110 may, when preprocessing the acquired medical data, calculate a shading change rate from the medical data, detect a region in which the calculated shading change rate is greater than or equal to a reference value as a target region for reading a rotator cuff tear, and segment the detected target region.

For example, the target region for reading a rotator cuff tear may include a location point of muscles and tendons surrounding a glenoid located between a scapula and a humerus.

In another case, the processor 110 may, when preprocessing the acquired medical data, firstly segment the target region for reading a rotator cuff tear from the acquired medical data, and secondly segment the target region for reading a rotator cuff tear from the medical data from which the target region has been firstly segmented.

Here, the processor 110 may, when firstly segmenting the target region, segment the target region based on a shading change of the medical data.

For example, the processor 110 may, when firstly segmenting the target region, calculate a shading change rate from the medical data, detect a region in which the calculated shading change rate is greater than or equal to a reference value as a target region for reading a rotator cuff tear, and segment the detected target region.

In addition, the processor 110 may, when secondly segmenting the target region, secondly segment the target region for reading a rotator cuff tear from the medical data, from which the target region has been firstly segmented, in the X-axis direction or the Y-axis direction.

Here, the processor 10 may, when secondly segmenting the target region, cut a target region for reading a rotator cuff tear from the medical data, from which the target region has been firstly segmented in the X-axis direction, such that the target region is secondly segmented into a plurality of target regions, or cut a target region in the Y-axis direction such that the target region is secondly segmented into a plurality of target regions.

In another case, the processor 110 may, when preprocessing the acquired medical data, firstly segment the target region for reading a rotator cuff tear from the acquired medical data, secondly segment the target region for reading a rotator cuff tear from the medical data, from which the target region has been firstly segmented, in the first direction, and thirdly segment the target region for reading a rotator cuff tear from the medical data, from which the target region has been firstly segmented, in the second direction.

Here, the processor 110 may, when firstly segmenting the target region, segment the target region based on a shading change of the medical data.

For example, the processor 110 may, when firstly segmenting the target region, calculate a shading change rate from the medical data, detect a region in which the calculated shading change rate is greater than or equal to a reference value as a target region for reading a rotator cuff tear, and firstly segment the detected target region.

Subsequently, the processor 110 may, when secondly segmenting the target region, secondly segment the target region for reading a rotator cuff tear from the medical data, from which the target region has been firstly segmented, in the X-axis direction.

Here, the processor 10 may, when secondly segmenting the target region, cut the target region for reading a rotator cuff tear from the medical data, from which the target region has been firstly segmented, in the X-axis direction to secondly segment the target region into a plurality of target regions.

In addition, the processor 110 may, when thirdly segmenting the target region, thirdly segment the target region for reading a rotator cuff tear from the medical data, from which the target region has been firstly segmented, in the Y-axis direction.

Here, the processor 10 may, when thirdly segmenting the target region, cut the target region for reading a rotator cuff tear from the medical data, from which the target region has been firstly segmented, in the Y-axis direction to thirdly segment the target region into a plurality of target regions.

Next, the processor 110 may, when reading a rotator cuff tear state, use a pre-trained neural network model to firstly read whether the rotator cuff tear state is a normal state or an abnormal state, and when a result of the reading is that the rotator cuff tear state is an abnormal state, secondly read whether the rotator cuff is in a partial tear state or a full-thickness tear state.

Here, the processor 110 may, when reading whether the rotator cuff is in a partial tear state, read whether the rotator cuff is in a partial tear state with a tear less than 50% or with a tear greater than or equal to 50%

For example, the processor 110 may, when the rotator cuff is in a partial tear state with a tear less than 50%, read that a surgery is not required, and when the rotator cuff is in a partial tear state with a tear greater than or equal to 50%, read that a surgery is required.

In addition, the processor 110 may, when reading whether the rotator cuff is in a full-thickness tear state, read whether the rotator cuff is in a full-thickness tear state with a one-tendon tear, whether the rotator cuff is in a full-thickness tear state with a two-tendon tear, or whether the rotator cuff is in a full-thickness tear state with a three-tendon tear.

Here, the processor 110 may, when a result of the reading is that the rotator cuff is in a full-thickness tear state with a one-tendon tear, read a first insurance fee code corresponding to the result, and when a result of the reading is that the rotator cuff is in a full-thickness tear state with a two-tendon tear, read a second insurance fee code corresponding to the result, and when a result of the reading is that the rotator cuff is in a full-thickness tear state with a three-tendon tear, read a third insurance fee code corresponding to the result.

In addition, the processor 110 may, when reading whether the rotator cuff is the full-thickness tear, read whether the rotator cuff is in a full-thickness tear state with a tendon tear less than 2.5 cm, whether the rotator cuff is in a full-thickness tear state with a tendon tear greater than or equal to 2.5 cm, or whether the rotator cuff is in a full-thickness tear state with a tendon tear greater than or equal to 2.5 cm, or a subscapularis tear requiring suturing.

Here, the processor 110 may, when a result of the reading is that the rotator cuff is in a full-thickness tear state with a tendon tear less than 2.5 cm, read a first insurance fee code corresponding to the result, and when a result of the reading is that the rotator cuff is in a full-thickness tear state with a tendon tear greater than or equal to 2.5 cm, read a second insurance fee code corresponding to the result, and when a result of the reading is that the rotator cuff is in a full-thickness tear state with a tendon tear greater than or equal to 2.5 cm or a subscapularis tear requiring, read a third insurance fee code corresponding to the result.

In addition, the neural network model according to the present invention may be pre-trained to, in response that the target region for reading a rotator cuff tear, which is segmented from the medical data, is input thereto, read a rotator cuff tear state.

In some cases, the neural network model according to the present invention may be pre-trained to, upon an input of the target region for reading a rotator cuff tear, read a rotator cuff tear state, and read whether to perform a surgery and read an insurance fee code based on a result of reading the rotator cuff tear state.

As an example, the neural network model may include a randomized controlled trial (RCT) model using a 3D U-Net, which is only an example, and the present invention is not limited thereto.

Subsequently, the processor 110 may, when generating the result information on the medical data, generate result information for visualizing the result of reading the rotator cuff tear state based on the read rotator cuff tear state.

For example, the result information for visualizing the result of reading the rotator cuff tear state may include at least one of a rotator cuff tear distance, a rotator cuff tear volume, an insurance fee code, or a rotator cuff tear area, which is only an example, and the present invention is not limited thereto.

Next, the processor 110 may, when preprocessing the acquired medical data, segment a target region for reading a fat degeneration of the rotator cuff from the acquired medical data.

Here, the processor 110 may, when segmenting the target region for reading a fat degeneration of the rotator cuff, use a pre-trained segmentation model to segment a rotator cuff region, and designate a region affecting classification as a region of interest (ROI).

For example, the pre-trained segmentation model may be a two-dimensional (2D) segmentation model including a 2D U-Net or a three-dimensional (3D) segmentation model including a 3D U-Net.

In addition, the designated ROI may include a supraspinatus (SS) region, an infraspinatus (IS) region, a teres minor (TM) region, and a subscapularis (Su) region, which is only an embodiment, and the present invention is not limited thereto.

In some cases, the processor 110 may, when preprocessing the acquired medical data, segment a target region for reading a fat degeneration of the rotator cuff based on a shading change of the medical data.

Here, the processor 110 may, when preprocessing the acquired medical data, calculate a shading change rate from the medical data, detect a region in which the calculated shading change rate is greater than or equal to a reference value as a target region for reading a fat degeneration of the rotator cuff, and segment the detected target region.

For example, the target region for reading the fat degeneration of the rotator cuff may include the supraspinatus (SS) region, the infraspinatus (IS) region, the teres minor (TM) region, and the subscapularis (Su) region, which is only an embodiment, and the present invention is not limited thereto.

In another case, the processor 110 may, when preprocessing the acquired medical data, firstly segment the target region for reading a fat degeneration of the rotator cuff from the acquired medical data, and secondly segment the target region for reading a fat degeneration of the rotator cuff from the medical data from which the target region has been firstly segmented.

Here, the processor 110 may, when firstly segmenting the target region, segment the target region based on a shading change of the medical data.

For example, the processor 110 may, when firstly segmenting the target region, calculate a shading change rate from the medical data, detect a region in which the calculated shading change rate is greater than or equal to a reference value as a target region for reading a fat degeneration of the rotator cuff, and firstly segment the detected target region.

In addition, the processor 110 may, when secondly segmenting the target region, secondly segment the target region into a plurality of target regions including a supraspinatus (SS) region, an infraspinatus (IS) region, a teres minor (TM) region, and a subscapularis (Su) region from the firstly segmented target region.

Next, the processor 110 may, when reading a rotator cuff fat degeneration state, use a pre-trained neural network model to firstly read whether the fat degeneration state of the rotator cuff is a normal state or an abnormal state, and when a result of the reading is that the fat degeneration state of the rotator cuff is an abnormal state, secondly read a fat degeneration level.

Here, the processor 110 may, when reading the fat degeneration level of the rotator cuff, calculate the degree of fat degeneration based on the area of fat present in the rotator cuff, and read the fat degeneration level based on the calculated degree of fat degeneration.

For example, the degree of fat degeneration may be calculated based on a formula expressed as (B–A)/B (B is the area of a rotator cuff, and A is the area excluding fat occupying the rotator cuff).

As another example, the degree of fat degeneration of the supraspinatus may be calculated based on a formula expressed as (B–A)/B (B is the total area of a supraspinatus region, and A is the area excluding fat occupying the supraspinatus region).

As another example, the degree of fat degeneration of the infraspinatus may be calculated based on a formula expressed as (B–A)/B (B is the total area of a infraspinatus region, and A is the area excluding fat occupying the infraspinatus region).

As another example, the degree of fat degeneration of the teres minor may be calculated based on a formula expressed as (B–A)/B (B is the total area of a teres minor region, and A is the area excluding fat occupying the teres minor region).

As another example, the degree of fat degeneration of the subscapularis may be calculated based on a formula expressed as (B–A)/B (B is the total area of a subscapularis region, and A is the area excluding fat occupying the subscapularis region).

Subsequently, the neural network model according to the present invention may be pre-trained to, in response that the target region for reading a fat degeneration of the rotator cuff, which is segmented from the medical data, is input thereto, read a fat degeneration state of the rotator cuff.

In some cases, the neural network model according to the present invention may be pre-trained to, upon an input of the target region for reading a fat degeneration of the rotator cuff, read a fat degeneration state of the rotator cuff, and calculate the degree of fat degeneration based on a result of reading the fat degeneration state of the rotator cuff to read a fat degeneration level.

In addition, the processor 110 may, when generating result information on the medical data, generate result information including a treatment guide based on the read fat degeneration state of the rotator cuff.

In another case, the processor 110 may, when generating result information on the medical data, classify a class for fat degeneration based on the read fat degeneration state of the rotator cuff, and generate result information including a treatment guide corresponding to the classified class.

In addition, the above described neural network model may be a deep neural network. Throughout this specification, a neural network and a network function may be used with the same meaning. A deep neural network (DNN) may refer to a neural network including a plurality of hidden layers in addition to an input layer and an output layer. By using a DNN, a latent structure of data may be identified. In other words, a latent structure (e.g., the type of an object included in a photo, contents and mood of text, and contents, mood of speech) of a photo, text, video, speech, or music may be identified. DNNs may include a convolutional neural network (CNN), a recurrent neural network (RNN), a restricted Boltzmann machine (RBM), a deep belief network (DBN), a Q network, an U network, Siamese network, and the like.

A CNN is a type of deep neural network and includes a neural network including a convolutional layer. A CNN is a type of multilayer perceptron designed to use minimal preprocessing. A CNN may be composed of one or more convolutional layers and artificial neural network layers coupled thereto. A CNN may additionally utilize weights and pooling layers. With such a structure, CNNs may fully utilize input data of a two-dimensional structure. A CNN may be used to recognize objects in images. A CNN may represent image data as a matrix having a dimension, and process the matrix. For example, in the case of image data encoded in red-green-blue (RGB), the image data may be represented as two-dimensional (in the case of a two-dimensional image) matrices for each R, G, and B color. That is, each pixel's color value in the image data may be represented as a matrix element, and the size of the matrix may be the same as the size of the image. Thus, image data may be represented by three 2D matrices (a three-dimensional data array).

In a convolutional neural network, a convolutional process (input/output of a convolutional layer) may be performed by moving a convolutional filter such that the convolutional filter is multiplied with matrix elements at each position of an image. A convolutional filter may be composed as an n*n matrix. A convolutional filter may be provided as a fixed shape filter, which is usually smaller than the total number of pixels in an image. That is, when an m*m image is input to a convolutional layer (e.g., a convolutional layer in which the size of a convolutional filter is n*n), a matrix representing n*n pixels including each pixel of the image may be subject to element-multiplication (i.e., multiplying corresponding elements of the matrices) with the convolutional filter. Such a multiplication with a convolutional filter allows a component that matches with the convolutional filter to be extracted from the image. For example, a 3*3 convolutional filter to extract a vertical linear component from an image may be constructed as [[0,1,0], [0,1,0], [0,1,0]]. When a 3*3 convolutional filter for extracting a vertical linear component from an image is applied to an input image, a vertical linear component matching with the convolutional filter may be extracted from the image and output. The convolutional layer may apply the convolutional filter to each matrix for each channel representing an image (i.e., R, G, B colors in the case of an R-G-B coded image). The convolutional layer may apply the convolutional filter to an input image to extract features matching with the convolutional filter from the input image. The filter value (i.e., the value of each element of the matrix) of the convolutional filter may be updated by backpropagation during a learning process of the CNN.

The output of the convolutional layer may be connected to a subsampling layer so that the output of the convolutional layer is simplified, thereby reducing memory usage and computational complexity. For example, when the output of the convolutional layer is input to a pooling layer with a 2*2 max pooling filter, the maximum value included in each 2*2 patch of pixels in the image may be output so that the image may be compressed. The above described pooling may be a method of outputting a minimum value of a patch or an average value of a patch, and any pooling method may be included in the present invention.

A CNN may include one or more convolutional layers and subsampling layers. A CAMM may extract features from an image by repeatedly performing a convolutional process and a subsampling process (e.g., the MAX pooling described above). Through an iterative convolutional process and subsampling process, a neural network may extract global features of an image.

The output of the convolutional layer or the subsampling layer may be input to a fully connected layer. A fully connected layer is a layer in which all neurons in one layer are connected to all neurons in a neighboring layer. A fully connected layer may refer to a structure in which all nodes of each layer are connected to all nodes of another layer in a neural network.

According to an embodiment of the present invention, the processor 110 may be provided as one or more cores, and may include a processor for data analysis and deep learning, such as a central processing unit (CPU) of a computing device, a general purpose graphics processing unit (GPGPU), a tensor processing unit (TPU), and the like. The processor 110 may read a computer program stored in the memory 130 and perform data processing for machine learning according to an embodiment of the present invention. According to an embodiment of the present invention, the processor 110 may perform a computation for training a neural network. The processor 110 may perform calculation for training a neural network, such as processing of input data for training in deep learning (DL), extraction of features from input data, calculation of errors, and update of neural network weights using backpropagation. At least one of the CPU, GPGPU, or TPU of the processor 110 may process learning of a network function. For example, the CPU and GPGPU may process learning of network functions and data classification using network functions. In addition, according to an embodiment of the present invention, learning of network functions and data classification using network functions may be processed using processors of a plurality of computing devices together. In addition, a computer program performed in a computing device according to an embodiment of the present invention may be a program executable by a CPU, GPGPU or TPU.

According to an embodiment of the present invention, the memory 130 may store a computer program for performing a shoulder disorder reading and providing a shoulder disorder reading result, and the stored computer program may be read and driven by the processor 120. The memory 130 may store any type of information generated or determined by the processor 110 and any type of information received by the network unit 150.

According to an embodiment of the present invention, the memory 130 may include at least one type of storage medium among a flash memory type storage medium, a hard disk type storage medium, a multimedia card micro type storage medium, a card type memory (e.g. a SD or an XD memory, etc.), a Random Access Memory (RAM), a Static Random Access Memory (SRAM), a Read-Only Memory (ROM), an Electrically Erasable Programmable Read-Only Memory (EEPROM), a Programmable Memory Read-Only Memory ((PROM)), a magnetic memory, a magnetic disk, or an optical disk. The computing device 100 may operate in association with a web storage that performs a storage function of the memory 130 on the Internet. The memory described above is only an example, and the present invention is not limited thereto.

The network unit 150 according to an embodiment of the present invention may transmit and receive shoulder disorder reading result information and the like to and from other computing devices, servers, and the like. In addition, the network unit 150 may enable communication between a plurality of computing devices such that operations for reading a shoulder disorder or training a model may be performed in a distributed manner in each of the plurality of computing devices. The network unit 150 may enable communication between a plurality of computing devices such that computation s for shoulder disorder reading or model training using a network function are processed in a distributed manner.

The network unit 150 according to an embodiment of the present invention may operate based on any type of wired or wireless communication technology currently used and implemented, such as short-range communication (near-field), long-range communication, wired communication, wireless communication, and the like, and may also be used in other networks.

The computing device 100 according to the present invention may further include an output unit and an input unit.

The output unit according to an embodiment of the present invention may display a user interface (UI) for providing a shoulder disorder reading result. The output unit may output any type of information generated or determined by the processor 110 and any type of information received by the network unit 150.

In one embodiment of the present invention, the output unit may include at least one of a liquid crystal display (LCD), a thin film transistor liquid crystal display (TFT LCD), an organic light-emitting diode (OLED), a flexible display, or a 3D display. Some of the display modules may be formed as a transparent type or a light transmissive type to allow the outside to be seen therethrough. Such a display module may be referred to as a transparent display module, and representative examples of the transparent display module may include a transparent OLED (TOLED) and the like.

The input unit according to an embodiment of the present invention may receive a user input. The input unit may include keys and/or buttons on a user interface for receiving user input, or physical keys and/or buttons. In response to a user input through the input unit, a computer program for controlling a display according to embodiments of the present invention may be executed.

The input unit according to embodiments of the present invention may detect a user's button manipulation or touch input to receive a signal, or may receive a user's speech or motion through a camera or microphone and convert the user's speech or motion into an input signal. For this, speech recognition technology or motion recognition technology may be used.

The input unit according to embodiments of the present invention may be implemented as an external input device connected to the computing device 100. For example, the input device may be at least one of a touch pad, a touch pen, a keyboard, or a mouse for receiving a user input, but this is only an example and the present invention is not limited thereto.

The input unit according to an embodiment of the present invention may recognize a user touch input. The input unit according to an embodiment of the present invention may be the same component as the output unit. The input unit may include a touch screen implemented to receive a user's selection input. The touch screen may use any one of a contact capacitive method, an infrared light sensing method, a surface ultrasonic (surface acoustic wave: SAW) method, a piezoelectric method, and a resistive film method. The detailed description of the touch screen is only an example according to an embodiment of the present invention, and various touch screen panels may be employed in the computing device 100. The input unit implemented as a touch screen may include a touch sensor. The touch sensor may be configured to convert a change in pressure applied to a specific portion of the input unit or a change in capacitance generated at a specific portion of the input unit into an electrical input signal. The touch sensor may be configured to detect not only the touched position and area, but also the pressure upon touch. Upon a touch input to the touch sensor, a corresponding signal(s) may be transmitted to a touch controller. The touch controller may process the signal(s) and then transmit corresponding data to processor 110. Accordingly, the processor 110 may recognize which area of the input unit has been touched.

In one embodiment of the present invention, a server may include other components for performing a server environment of the server. The server may include any type of apparatus. The server may be a digital device equipped with a processor and a memory, such as a laptop computer, a notebook computer, a desktop computer, a web pad, or a mobile phone, with a computing power.

A server (not shown) performing an operation for providing a user terminal with a user interface displaying a result of shoulder disorder reading according to an embodiment of the present invention may include a network unit, a processor, and a memory.

The server may generate a user interface according to embodiments of the present invention. The server may be a computing system that provides information to clients (e.g., user terminals) over a network. The server may transmit the generated user interface to the user terminal. In this case, the user terminal may be any type of computing device 100 capable of accessing the server. The processor of the server may transmit the user interface to the user terminal through the network unit. The server according to embodiments of the present invention may be, for example, a cloud server. The server may be a web server that processes services. The types of servers described above are examples only and are not limited thereto.

As described above, the present invention is implemented to preprocess medical data to segment a target region for reading a rotator cuff tear, and input the target region to a pre-trained neural network model to read a rotator cuff tear state, thereby increasing the accuracy in reading a rotator cuff tear.

In addition, as described above, the present invention is implemented to preprocess medical data to segment a target region for reading a fat degeneration of a rotator cuff, and input the target region to a pre-trained neural network model to read a fat degeneration state of the rotator cuff, thereby increasing the accuracy in reading a fat degeneration of a rotator cuff.

Figure 2:
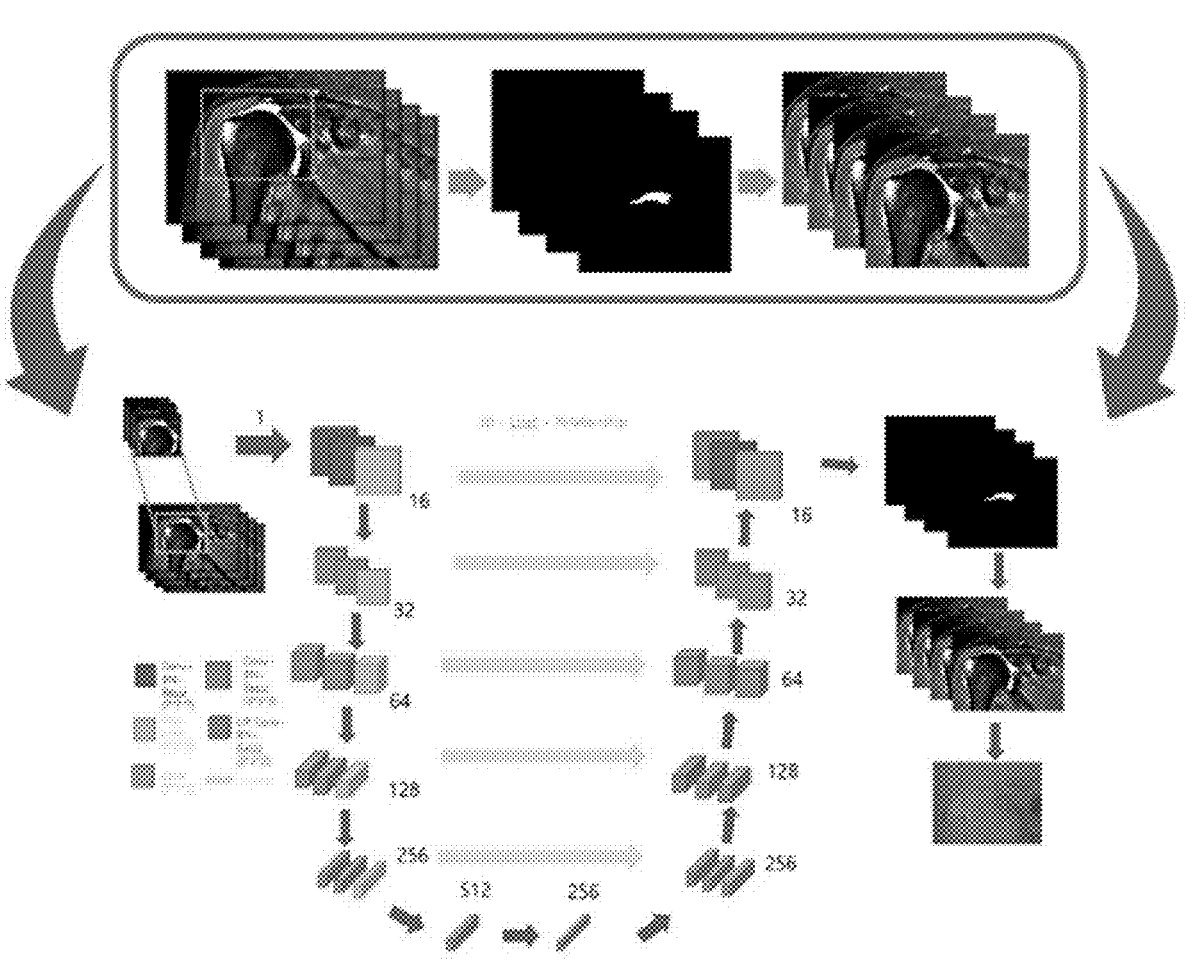
FIG. 2 is a schematic diagram illustrating a network function for reading a shoulder disorder, according to an embodiment of the present invention.

FIG. 2 is a schematic diagram illustrating a network function for reading a shoulder disorder, according to an embodiment of the present invention.

Referring to FIG. 2, the present invention may acquire medical data including a shoulder image, preprocess the acquired medical data, input the preprocessed medical data into a pre-trained neural network model to read a rotator cuff tear state, and generate result information on the medical data based on the read rotator cuff tear state.

Here, the present invention may use a 3D segmentation model including a pre-trained 3D U-Net to segment a rotator cuff region, and designate a region affecting classification as an ROI.

For example, the ROI may include a location point of muscles and tendons surrounding a glenoid located between a scapula and a humerus, which is only one embodiment, and the present invention is not limited thereto.

In addition, the neural network model according to the present invention may include a RCT model using a 3D U-Net.

Here, the neural network model according to the present invention may be pre-trained to, in response that a target region for reading a rotator cuff tear, which is segmented from the medical data, is input thereto, read a rotator cuff tear state, and based on a result of reading the rotator cuff tear state, read whether to perform a surgery and read an insurance fee code corresponding to the result of reading the rotator cuff tear state.

Subsequently, the present invention may, through a pre-trained neural network model, firstly read whether the rotator cuff tear state is a normal state or an abnormal state, and when a result of the reading is that the rotator cuff tear state is an abnormal state, secondly read whether the rotator cuff is in a partial tear state or a full-thickness tear state.

In addition, the present invention may generate result information for visualizing the result of reading the rotator cuff tear state based on the read rotator cuff tear state.

Figure 3:
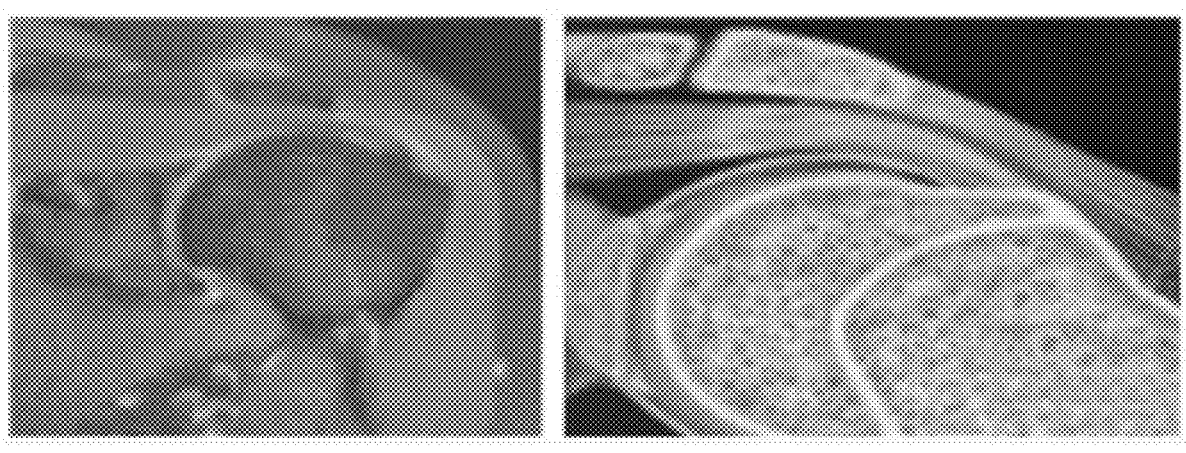
FIGS. 3 and 4 are diagrams showing segmented images of a rotator cuff region for reading a rotator cuff tear state, according to an embodiment of the present invention.
Figure 4:
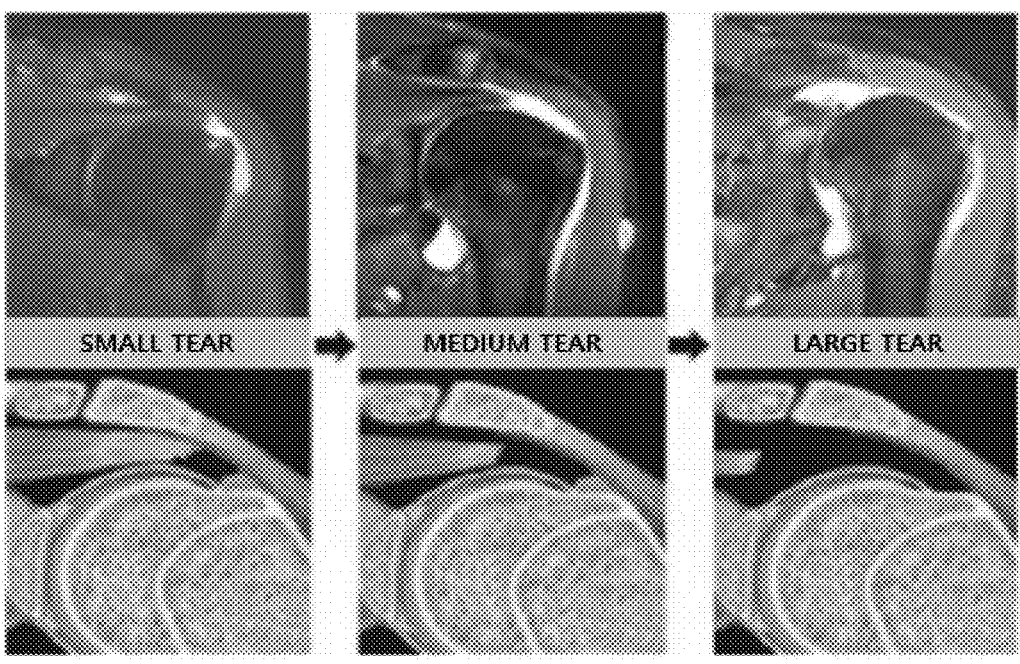

FIGS. 3 and 4 are diagrams showing segmented images of a rotator cuff region for reading a rotator cuff tear state, according to an embodiment of the present invention.

Referring to FIGS. 3 and 4, the present invention may, upon input of a preprocessed segmented image of medical data, through a pre-trained neural network model, firstly read whether a rotator cuff tear state is a normal state or an abnormal state, and when a result of the reading is that the rotator cuff tear state is an abnormal state, secondly read whether the rotator cuff is in a partial tear state or a full-thickness tear state.

The present invention may, upon a preprocessed segmented image of medical data being input into a pre-trained neural network model, read that the rotator cuff tear state is a normal state, as shown in FIG. 3.

In addition, the present invention may, upon a preprocessed segmented image of medical data being input into a pre-trained neural network model, read that the rotator cuff tear state is an abnormal state, as shown in FIG. 4.

Here, the present invention may, when reading whether the rotator cuff is in a partial tear state, read that a surgery is not required in response that the rotator cuff is in a partial tear state with a tear less than 50%, and read that a surgery is required in response that the rotator cuff is in a partial tear state with a tear greater than or equal to 50%.

In addition, when reading whether the rotator cuff is in a full-thickness tear state, the present invention may, in response that the rotator cuff is in a full-thickness tear state with a one-tendon tear (i.e., a small tear), read a first insurance fee code corresponding thereto, and in response that the rotator cuff is in a full-thickness tear state with a two-tendon tear (i.e., a medium tendon), read a second insurance fee code corresponding thereto, and in response that the rotator cuff is in a full-thickness tear state with a three-tendon tear (i.e., a large tear), read a third insurance fee code corresponding thereto.

Figure 5:
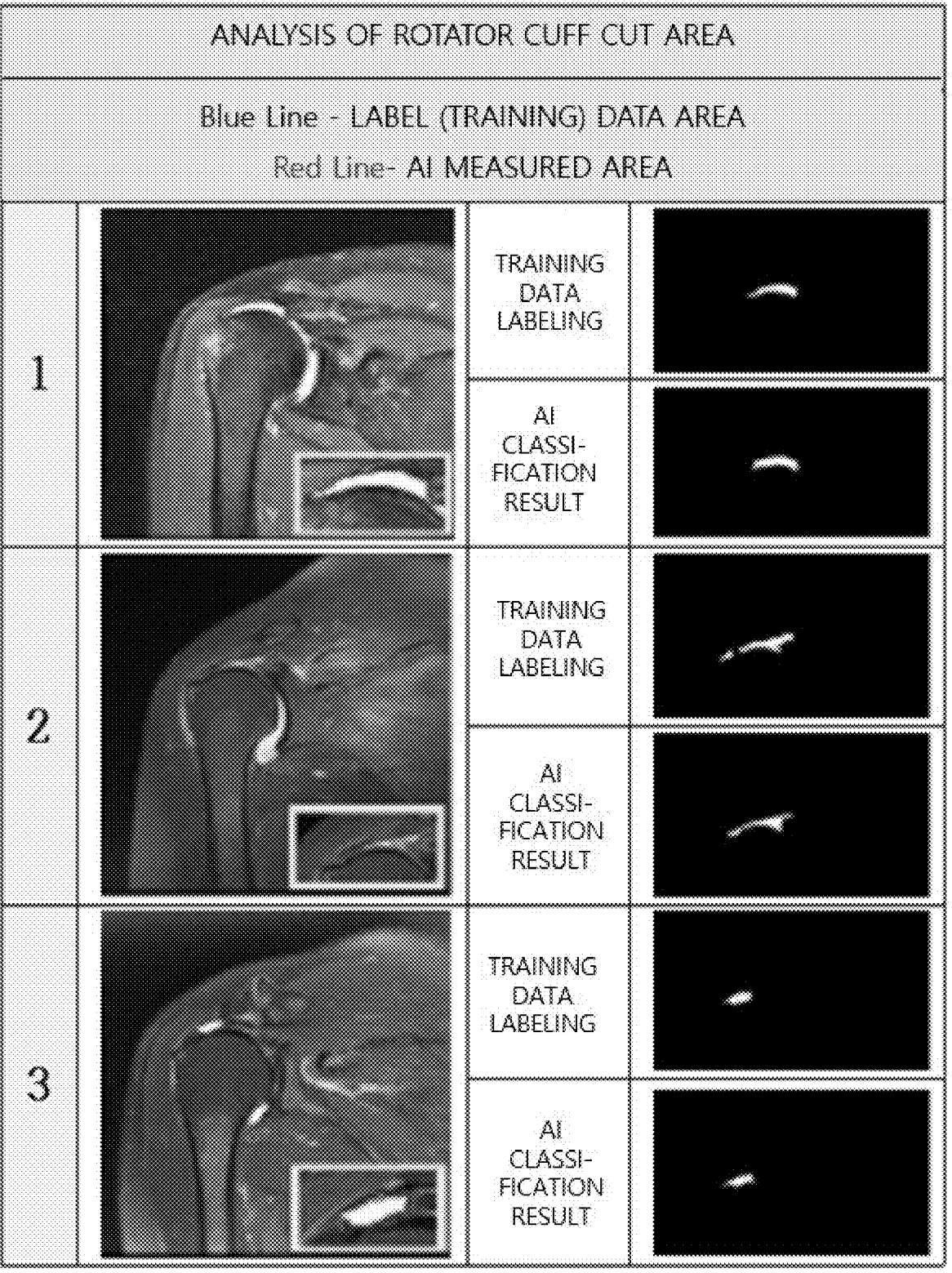
FIG. 5 is a diagram showing preprocessed images of a rotator cuff tear area, according to an embodiment of the present invention.

FIG. 5 is a diagram showing preprocessed images of a rotator cuff tear area, according to an embodiment of the present invention.

Referring to FIG. 5, the present invention may, when preprocessing the acquired medical data, segment a target region for reading a rotator cuff tear based on a shading change of the medical data.

Here, the present invention may, when preprocessing the acquired medical data, calculate a shading change rate from the medical data, detect a region in which the calculated shading change rate is greater than or equal to a reference value as a target region for reading a rotator cuff tear, and segment the detected target region.

In another case, the present invention may, when preprocessing the acquired medical data, firstly segment the target region for reading a rotator cuff tear from the acquired medical data, and secondly segment the target region for reading a rotator cuff tear from the medical data from which the target region has been firstly segmented.

Here, the present invention may, when firstly segmenting the target region, calculate a shading change rate from the medical data, detect a region in which the calculated shading change rate is greater than or equal to a reference value as a target region for reading a rotator cuff tear, and firstly segment the detected target region.

In addition, the present invention may, when secondly segmenting the target region, cut the target region for reading a rotator cuff tear from the medical data, from which the target region has been firstly segmented in the X-axis direction, such that the target region is secondly segmented into a plurality of target regions, or cut the target region for reading a rotator cuff tear from the medical data, from which the target region has been firstly segmented, in the Y-axis direction such that the target region is secondly segmented into a plurality of target regions.

In another case, the present invention may, when preprocessing the acquired medical data, firstly segment the target region for reading a rotator cuff tear from the acquired medical data, secondly segment the target region for reading a rotator cuff tear from the medical data, from which the target region has been firstly segmented, in the first direction, and thirdly segment the target region for reading a rotator cuff tear from the medical data, from which the target region has been firstly segmented, in the second direction.

Here, the present invention may, when firstly segmenting the target region, calculate a shading change rate from the medical data, detect a region in which the calculated shading change rate is greater than or equal to a reference value as a target region for reading a rotator cuff tear, and firstly segment the detected target region.

Subsequently, the present invention may, when secondly segmenting the target region, cut the target region for reading a rotator cuff tear from the medical data, from which the target region has been firstly segmented, in the X-axis direction to secondly segment the target region into a plurality of target regions.

In addition, the present invention may, when thirdly segmenting the target region, cut the target region for reading a rotator cuff tear from the medical data, from which the target region has been firstly segmented, in the Y-axis direction to thirdly segment the target region into a plurality of target regions.

Figure 6:
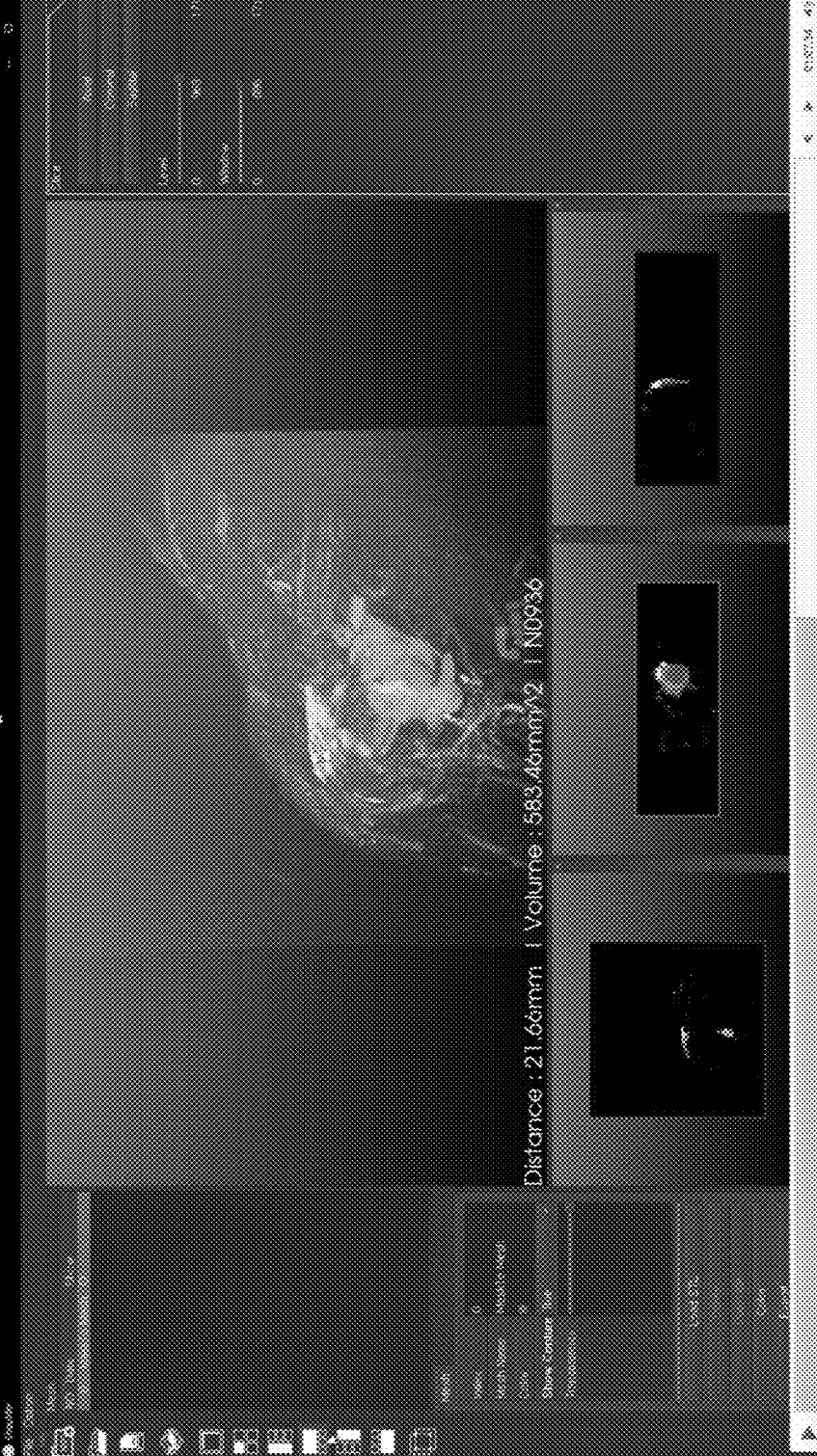
FIG. 6 is a diagram showing result information for visualizing reading of a rotator cuff tear state, according to an embodiment of the present invention.

FIG. 6 is a diagram showing result information for visualizing reading of a rotator cuff tear state, according to an embodiment of the present invention.

Referring to FIG. 6, the present invention may generate result information for visualizing a result of reading the rotator cuff tear state based on the read rotator cuff tear state.

For example, the result information for visualizing the result of reading the rotator cuff tear state may include at least one of a rotator cuff tear distance, a rotator cuff tear volume, an insurance fee code, or a rotator cuff tear area, which is indicated in a specific color. However, this is only an example, and the present invention is not limited thereto.

Figure 7:
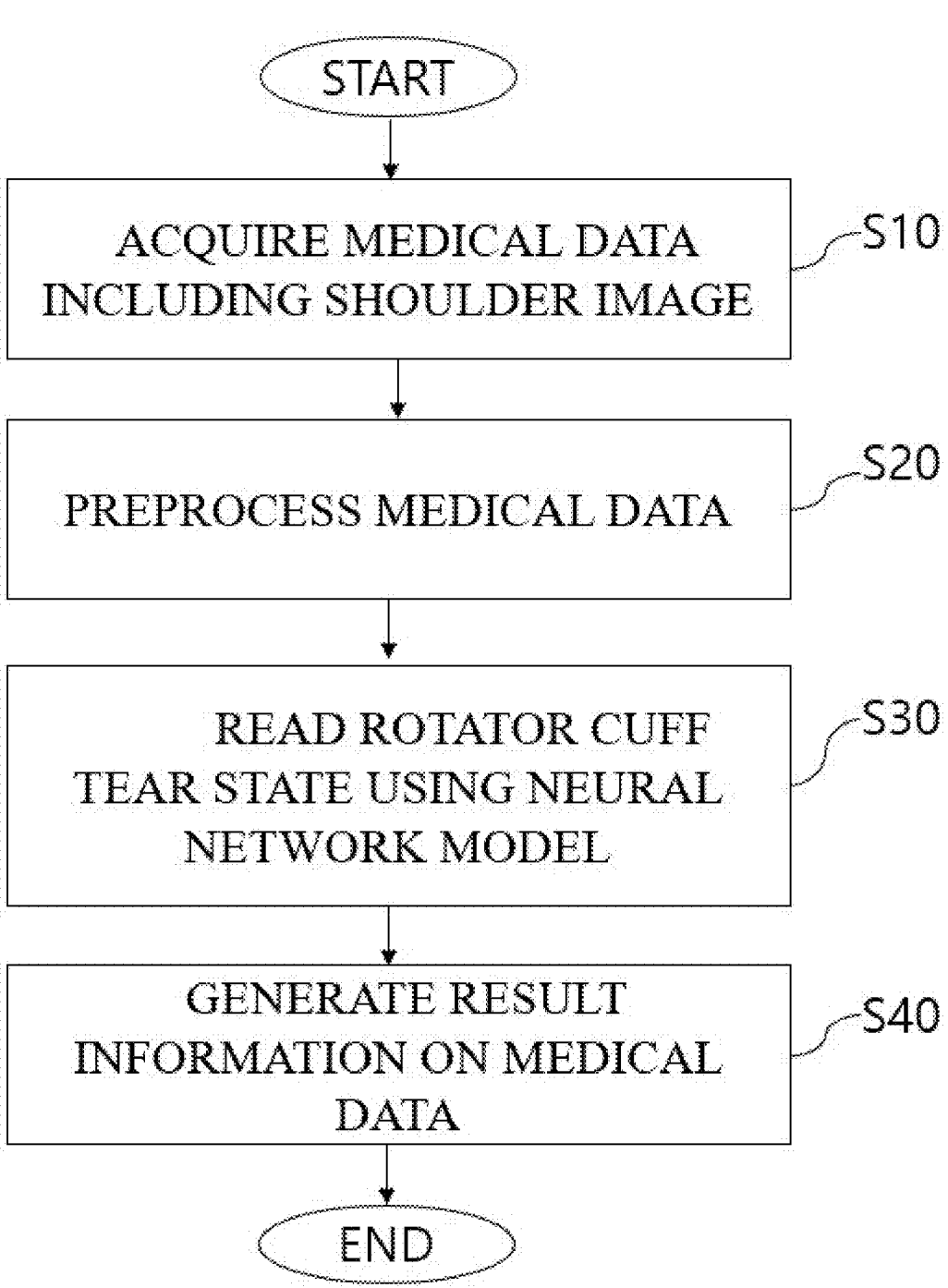
FIG. 7 is a flowchart for describing a method of reading a shoulder disorder, according to an embodiment of the present invention.

FIG. 7 is a flowchart for describing a method of reading a shoulder disorder, according to an embodiment of the present invention.

Referring to FIG. 7, the present invention may acquire medical data including a shoulder image (S10).

In addition, the present invention may preprocess the acquired medical data (S20).

Here, the present invention may segment a rotator cuff region using a pre-trained segmentation model, and designate a region affecting classification as an ROI.

In some cases, the present invention may segment a target region for reading a rotator cuff tear based on a shading change of the medical data.

In another case, the present invention may firstly segment the target region for reading a rotator cuff tear from the acquired medical data, and secondly segment the target region for reading a rotator cuff tear from the medical data from which the target region has been firstly segmented.

Here, the present invention may, when firstly segmenting the target region, segment the target region based on a shading change of the medical data, and secondly segment the target region for reading a rotator cuff tear from the medical data, from which the target region has been firstly segmented, in the X-axis direction or the Y-axis direction.

In another case, the present invention may firstly segment a target region for reading a rotator cuff tear from the acquired medical data, secondly segment the target region for reading a rotator cuff tear from the medical data, from which the target region has been firstly segmented, in the first direction, and thirdly segment the target region for reading a rotator cuff tear from the medical data, from which the target region has been firstly segmented, in the second direction.

Here, the present invention may firstly segment the target region based on a shading change of the medical data, secondly segment the target region for reading a rotator cuff tear from the firstly segmented medical data in the X-axis direction, and thirdly segment the target region for reading a rotator cuff tear from the firstly segmented medical data in the Y-axis direction.

Next, the present invention may input the preprocessed medical data to the pre-trained neural network model to read a rotator cuff tear state (S30).

Here, the present invention may, through the pre-trained neural network model, firstly read whether the rotator cuff tear state is a normal state or an abnormal state, and when a result of the reading is that the rotator cuff tear state is an abnormal state, secondly read whether the rotator cuff is in a partial tear state or a full-thickness tear state.

Subsequently, the present invention may generate result information on the medical data based on the read rotator cuff tear state (S40).

Here, the present invention may generate result information for visualizing the result of reading the rotator cuff tear state based on the read rotator cuff tear state.

For example, the result information for visualizing the result of reading the rotator cuff tear state may include at least one of a rotator cuff tear distance, a rotator cuff tear volume, an insurance fee code, or a rotator cuff tear area, which is only an example, and the present invention is not limited thereto.

As described above, the present invention preprocesses medical data to segment a target region for reading a rotator cuff tear, and inputs the target region to a pre-trained neural network model to read a rotator cuff tear state, thereby increasing the accuracy in reading a rotator cuff tear.

FIG. 8 is a schematic diagram illustrating a network function for reading a shoulder disorder, according to another embodiment of the present invention.

Referring to FIG. 8, the present invention may acquire medical data including a shoulder image, preprocess the acquired medical data, inputting the preprocessed medical data into a pre-trained neural network model to read a fat degeneration of a rotator cuff, and generate result information on the medical data based on the read fat degeneration state of the rotator cuff.

Here, the present invention may use a 3D segmentation model including a pre-trained 3D U-Net to segment a rotator cuff region, and designate a region affecting classification as an ROI.

For example, the designated ROI may include the supraspinatus (SS) region, the infraspinatus (IS) region, the teres minor (TM) region, and the subscapularis (Su) region, which is only an embodiment, and the present invention is not limited thereto.

Subsequently, the present invention may, through a pre-trained neural network model, firstly read whether the fat degeneration state of the rotator cuff is a normal state or an abnormal state, and when a result of the reading is that the fat degeneration state of the rotator cuff is an abnormal state, secondly read a fat degeneration level.

Here, the present invention may, when reading the fat degeneration level of the rotator cuff, calculate the degree of fat degeneration based on the area of fat present in the rotator cuff, and read the fat degeneration level based on the calculated degree of fat degeneration.

As described above, the neural network model according to the present invention may be pre-trained to, in response that the target region for reading a fat degeneration of the rotator cuff, which is segmented from the medical data, is input thereto, read a fat degeneration state of the rotator cuff.

In some cases, the neural network model according to the present invention may be pre-trained to, in response that the target region for reading a fat degeneration of the rotator cuff, which is segmented from the medical data, is input thereto, read a fat degeneration state of the rotator cuff, and calculate the degree of fat degeneration based on a result of reading the fat degeneration state of the rotator cuff to read a fat degeneration level.

In addition, the present invention may generate result information including a treatment guide based on the read fat degeneration state of the rotator cuff.

FIG. 9 is a diagram showing segmented images for reading a fat degeneration level of a rotator cuff, according to another embodiment of the present invention.

Referring to FIG. 9, the present invention may, through a pre-trained neural network model, firstly read whether the fat degeneration state of the rotator cuff is a normal state or an abnormal state, and when a result of the reading is that the fat degeneration state of the rotator cuff is an abnormal state, secondly read a fat degeneration level.

The present invention may, in response to a preprocessed segmented image of medical data being input to the pre-trained neural network model, read the fat degeneration state of the rotator cuff as a normal state and read the fat degeneration level as Grade 0, as shown in FIG. 9.

In addition, the present invention may, in response to a preprocessed segmented image of medical data being input to the pre-trained neural network model, read the fat degeneration state of the rotator cuff as an abnormal state and read the fat degeneration level as Grade 0 to Grade 4 according to the degree of fat degeneration, as shown in FIG. 9.

Here, the present invention may, when reading the fat degeneration level of the rotator cuff, calculate the degree of fat degeneration based on the area of fat present in the rotator cuff, and read the fat degeneration level based on the calculated degree of fat degeneration.

For example, the degree of fat degeneration may be calculated based on a formula expressed as (B–A)/B (B is the area of a rotator cuff, and A is the area excluding fat occupying the rotator cuff).

For example, as shown in FIG. 9, the fat degeneration level of Grade 1 is a case in which a fat layer is slightly present in the rotator cuff region, the fat degeneration level of Grade 2 is a case in which fat is less than muscle in the rotator cuff region, the fat degeneration level of Grade 3 is a case in which fat is as much as muscle in the rotator cuff region, and the fat degeneration level of Grade 4 is a case in which fat is more than muscle in the rotator cuff region.

FIG. 10 is a diagram showing a preprocessed image of a fat degeneration area of a rotator cuff, according to another embodiment of the present invention.

Referring to FIG. 10, the present invention may, when preprocessing the acquired medical data, segment a target region for reading a fat degeneration of the rotator cuff based on a shading change of the medical data.

Here, the present invention may, when preprocessing the acquired medical data, calculate a shading change rate from the medical data, detect a region in which the calculated shading change rate is greater than or equal to a reference value as a target region for reading a fat degeneration of the rotator cuff, and segment the detected target region.

In another case, the present invention may, when preprocessing the acquired medical data, firstly segment the target region for reading a fat degeneration of the rotator cuff from the acquired medical data, and secondly segment the target region for reading a fat degeneration of the rotator cuff from the firstly segmented target region Here, the processor 110 may, when firstly segmenting the target region, segment the target region based on a shading change of the medical data, and when secondly segmenting the target region, secondly segment the target region from the firstly segmented target region into a plurality of target regions including a supraspinatus (SS) region, an infraspinatus (IS) region, a teres minor (TM) region, and a subscapularis (Su) region.

Next, when reading a rotator cuff fat degeneration state, the present invention may, through a pre-trained neural network model, firstly read whether the fat degeneration state of the rotator cuff is a normal state or an abnormal state, and when a result of the reading is that the fat degeneration state of the rotator cuff is an abnormal state, secondly read a fat degeneration level.

Here, the present invention may, when reading the fat degeneration level of the rotator cuff, calculate the degree of fat degeneration based on the area of fat present in the rotator cuff, and read the fat degeneration level based on the calculated degree of fat degeneration.

FIGS. 11 and 12 are diagram s showing preprocessed images for describing a process of calculating the degree of fat degeneration of a rotator cuff, according to another embodiment of the present invention.

Referring to FIGS. 11 and 12, the present invention may read whether the fat degeneration state of the rotator cuff is a normal state or an abnormal state through a pre-trained neural network model.

Here, the present invention may, when a result of reading is that the fat degeneration state of the rotator cuff is a normal state, read the fat degeneration level as Grade 0, as shown in FIG. 11.

However, the present invention may, when a result of reading is that the fat degeneration state of the rotator cuff is an abnormal state, calculate the degree of fat degeneration (%) based on the area of fat present in the rotator cuff, and read the fat degeneration level based on the calculated degree of fat degeneration, as shown in FIG. 12.

For example, the degree of fat degeneration may be calculated based on a formula expressed as (B–A)/B (B is the area of a rotator cuff, and A is the area excluding fat occupying the rotator cuff).

As another example, the degree of fat degeneration of the supraspinatus may be calculated based on a formula expressed as (B–A)/B (B is the total area of a supraspinatus region, and A is the area excluding fat occupying the supraspinatus region).

As another example, the degree of fat degeneration of the infraspinatus may be calculated based on a formula expressed as (B–A)/B (B is the total area of an infraspinatus region, and A is the area excluding fat occupying the infraspinatus region).

As another example, the degree of fat degeneration of the teres minor may be calculated based on a formula expressed as (B–A)/B (B is the total area of a teres minor region, and A is the area excluding fat occupying the teres minor region).

As another example, the degree of fat degeneration of the subscapularis may be calculated based on a formula expressed as (B–A)/B (B is the total area of a subscapularis region, and A is the area excluding fat occupying the subscapularis region).

As described above, the neural network model according to the present invention may be pre-trained to, upon an input of the target region for reading a fat degeneration of the rotator cuff, read the fat degeneration state of the rotator cuff, and calculate the degree of fat degeneration based on a result of reading the fat degeneration state of the rotator cuff to read a fat degeneration level.

FIG. 13 is a flowchart for describing a method of reading a shoulder disorder, according to another embodiment of the present invention.

Referring to FIG. 13, the present invention may acquire medical data including a shoulder image (S50).

In addition, the present invention may preprocess the acquired medical data (S60).

Here, the present invention may segment a fat degeneration area of a rotator cuff using a pre-trained segmentation model, and designate a region affecting classification as an ROI.

In some cases, the present invention may segment a target region for reading a fat degeneration of the rotator cuff based on a shading change of the medical data.

Here, the present invention may calculate a shading change rate from the medical data, detect a region in which the calculated shading change rate is greater than or equal to a reference value as a target region for reading a fat degeneration of the rotator cuff, and segment the detected target region.

In another case, the present invention may firstly segment the target region for reading a fat degeneration of the rotator cuff from the acquired medical data, and secondly segment the target region for reading a fat degeneration of the rotator cuff from the firstly segmented target region.

Here, the present invention may, when firstly segmenting the target region, segment the target region based on a shading change of the medical data, and when secondly segmenting the target region, secondly segment the target region into a plurality of target regions including a supraspinatus (SS) region, an infraspinatus (IS) region, a teres minor (TM) region, and a subscapularis (Su) region from the firstly segmented target region.

Next, the present invention may input the preprocessed medical data to the pre-trained neural network model to read a fat degeneration of the rotator cuff (S70).

Here, the present invention may, through the pre-trained neural network model, firstly read whether the fat degeneration state of the rotator cuff is a normal state or an abnormal state, and when a result of the reading is that the fat degeneration state of the rotator cuff is an abnormal state, secondly read a fat degeneration level.

Here, the present invention may, when reading the fat degeneration level of the rotator cuff, calculate the degree of fat degeneration based on the area of fat present in the rotator cuff, and read the fat degeneration level based on the calculated degree of fat degeneration.

Subsequently, the present invention may generate result information on the medical data based on the read fat degeneration state of the rotator cuff (S80).

Here, the present invention may generate result information including a treatment guide based on the read fat degeneration state of the rotator cuff.

In some cases, the present invention may classify a class for fat degeneration based on the read fat degeneration state of the rotator cuff, and generate result information including a treatment guide corresponding to the classified class.

As described above, the present invention preprocesses medical data to segment a target region for reading a fat degeneration of a rotator cuff, and input the target region to a pre-trained neural network model to read a fat generation state of the rotator cuff, thereby increasing the accuracy in reading a fat generation of a rotator cuff.

The method according to an embodiment of the present invention described above may be implemented as a program (or application) and stored in a medium to be executed in combination with a server, which is hardware.

The program may include code coded in a computer language, such as C, C++, Java, another machine language, etc., that can be read by a processor (e.g., a central processing unit (CPU)) of a computer through a device interface of the computer in order for the computer to read the program and execute the methods implemented as the program. The code may include functional code that is related to a function that defines functions needed to execute the methods and may include execution procedure-related control code needed to cause the processor of the computer to execute the functions according to a predetermined procedure. In addition, the code may further include memory reference-related code indicating a location (an address) of an internal or external memory of the computer where additional information or media needed to cause the processor of the computer to execute the functions should be referenced. In addition, when the processor of the computer needs to communicate with any other computer or server, etc. at a remote site, to perform the above-described functions, the code may further include communication-related code such as how to communicate with any other computer or server at a remote site and what information or media should be transmitted or received during communication.

The storage medium is not a medium that stores data for a short period of time, such as a register, cache, memory, etc., but is a medium that stores data semi-permanently and can be read by a device. Specifically, examples of the storage medium may include a read-only memory (ROM), a random-access memory (RAM), a compact disc (CD)-ROM, a magnetic tape, a floppy disk, an optical data storage device, etc., but the storage medium is not limited thereto. That is, the program may be stored in various recording media on various servers accessible by the computer or on various recording media on the computer of the user. In addition, the media may be distributed over computer systems connected through a network so that computer-readable code may be stored in a distributed manner.

The operations of the method or algorithm described in connection with the embodiment of the present invention may be implemented directly in hardware, implemented in a software module executed by hardware, or implemented in a combination thereof. Software modules may reside in a RAM, a ROM, an Erasable Programmable ROM (EPROM), an Electrically Erasable Programmable ROM (EEPROM), a flash memory, a hard disk, a removable disk, a CD-ROM, or any other form of computer-readable recording medium known in the art to which the present invention pertains.

As is apparent from the above, according to the present invention, the accuracy in reading a rotator cuff tear can be increased by preprocessing medical data to segment a target region for reading a rotator cuff tear, and inputting the target region into a pre-trained neural network model to read a tear state of a rotator cuff.

According to the present invention, the accuracy in reading a fat degeneration of a rotator cuff can be increased by preprocessing medical data to segment a target region for reading a fat degeneration of a rotator cuff, and inputting the target region into a pre-trained neural network model to read a fat degeneration state of a rotator cuff.

The effects of the present invention are not limited to those described above, and other effects not described above will be clearly understood by those skilled in the art from the above detailed description.

Although the present invention has been described in detail above with reference to the exemplary embodiments, those of ordinary skill in the technical field to which the present invention pertains should be able to understand that various modifications and alterations may be made without departing from the technical spirit or essential features of the present invention. Therefore, it should be understood that the disclosed embodiments are not limiting but illustrative in all aspects.

What is claimed is:

1. A method of reading a shoulder disorder, which is a method performed by an apparatus for reading a shoulder disorder, the method comprising:

acquiring medical data including a shoulder image;

preprocessing the acquired medical data;

inputting the preprocessed medical data into a pre-trained neural network model, and performing reading of a tear state of a rotator cuff or reading of a fat degeneration state of the rotator cuff, wherein the reading of the tear state of the rotator cuff comprises:

calculating a shading change rate of each region of the shoulder image;

detecting a target region in which the calculated shading change rate is greater than or equal to a reference value;

performing a first segmentation of the target region from the shoulder image;

performing a second segmentation of the target region into a plurality of regions by dividing the target region in an X-axis direction or a Y-axis direction; and reading the tear state of the rotator cuff in each of the plurality of regions of the second segmentation, and wherein the reading of the fat degeneration state of the rotator cuff comprises:

calculating the shading change rate of each region of the shoulder image;

detecting the target region in which the calculated shading change rate is greater than or equal to the reference value;

performing the first segmentation of the target region from the shoulder image;

performing a third segmentation of the target region into a plurality of regions including a supraspinatus (SS) region, an infraspinatus (IS) region, a teres minor (TM) region, and a subscapularis (Su) region; and reading the fat degeneration state of the rotator cuff in each of the plurality of regions of the third segmentation; and generating result information on the medical data based on the read tear state of the rotator cuff or the read fat degeneration state of the rotator cuff.

2. The method of claim 1, wherein the detecting of the target region is performed by using a pre-learned segmentation model.

3. The method of claim 1, wherein the reading of the tear state of the rotator cuff includes, through the pre-trained neural network model:

firstly reading whether the tear state of the rotator cuff is a normal state or an abnormal state; and when a result of the reading is that the tear state of the rotator cuff is an abnormal state, secondly reading whether the rotator cuff is in a partial tear state or a full-thickness tear state.

4. The method of claim 3, wherein the reading of whether the rotator cuff is in the partial tear state includes reading whether the rotator cuff is in a partial tear state with a tear less than 50% or the rotator cuff is in a partial tear state with a tear greater than or equal to 50%.

5. The method of claim 4, wherein the reading of whether the rotator cuff is in the partial tear state includes:

when the rotator cuff is in a partial tear state with a tear less than 50%, reading that a surgery is not required; and when the rotator cuff is in a partial tear state with a tear greater than or equal to 50%, reading that a surgery is required.

6. The method of claim 3, wherein the reading of whether the rotator cuff is in the full-thickness tear state includes reading whether the rotator cuff is in a full-thickness tear state with a one-tendon tear, whether the rotator cuff is in a full-thickness tear state with a two-tendon tear, or whether the rotator cuff is in a full-thickness tear state with a three-tendon tear.

7. The method of claim 6, wherein the reading of whether the rotator cuff is in the full-thickness tear state includes:

when a result of the reading is that the rotator cuff is in a full-thickness tear state with a one-tendon tear, reading a first insurance fee code corresponding to the result;

when a result of the reading is that the rotator cuff is in a full-thickness tear state with a two-tendon tear, reading a second insurance fee code corresponding to the result; and when a result of the reading is that the rotator cuff is in a full-thickness tear state with a three-tendon tear, reading a third insurance fee code corresponding to the result.

8. A non-transitory computer readable recording medium storing a computer program, the computer program that, when executed by one or more processors, performs the following operations for reading a shoulder disorder, the operations comprising:

an operation of acquiring medical data including a shoulder image;

an operation of preprocessing the acquired medical data;

an operation of inputting the preprocessed medical data into a pre-trained neural network model, and performing reading of a tear state of a rotator cuff or reading of a fat degeneration of the rotator cuff, wherein the reading of the tear state of the rotator cuff comprises:

calculating a shading change rate of each region of the shoulder image;

detecting a target region in which the calculated shading change rate is greater than or equal to a reference value;

performing a first segmentation of the target region from the shoulder image;

performing a second segmentation of the target region into a plurality of regions by dividing the target region in an X-axis direction or a Y-axis direction; and reading the tear state of the rotator cuff in each of the plurality of regions of the second segmentation, and wherein the reading of the fat degeneration state of the rotator cuff comprises:

calculating the shading change rate of each region of the shoulder image;

detecting the target region in which the calculated shading change rate is greater than or equal to the reference value;

performing the first segmentation of the target region from the shoulder image;

performing a third segmentation of the target region into a plurality of regions including a supraspinatus (SS) region, an infraspinatus (IS) region, a teres minor (TM) region, and a subscapularis (Su) region; and reading the fat degeneration state of the rotator cuff in each of the plurality of regions of the third segmentation; and an operation of generating result information on the medical data based on the read tear state of the rotator cuff or the read fat degeneration state of the rotator cuff.

9. A computing device for providing a method of reading a shoulder disorder, the computing device comprising:

a processor including one or more cores; and a memory, wherein the processor is configured to:

acquire medical data including a shoulder image;

preprocess the acquired medical data;

input the preprocessed medical data into a pre-trained neural network model, and perform reading of a tear state of a rotator cuff or reading of a fat degeneration of the rotator cuff, wherein the reading of the tear state of the rotator cuff comprises:

calculating a shading change rate of each region of the shoulder image;

detecting a target region in which the calculated shading change rate is greater than or equal to a reference value;

performing a first segmentation of the target region from the shoulder image;

performing a second segmentation of the target region into a plurality of regions by dividing the target region in an X-axis direction or a Y-axis direction; and reading the tear state of the rotator cuff in each of the plurality of regions of the second segmentation, and wherein the reading of the fat degeneration state of the rotator cuff comprises:

calculating the shading change rate of each region of the shoulder image;

detecting the target region in which the calculated shading change rate is greater than or equal to the reference value;

performing the first segmentation of the target region from the shoulder image;

performing a third segmentation of the target region into a plurality of regions including a supraspinatus (SS) region, an infraspinatus (IS) region, a *teres minor* (TM) region, and a subscapularis (Su) region; and reading the fat degeneration state of the rotator cuff in each of the plurality of regions of the third segmentation; and generate result information on the medical data based on the read tear state of the rotator cuff or the read fat degeneration state of the rotator cuff.

10. The method of claim 1, wherein the reading of the fat degeneration state of the rotator cuff includes, through the pre-trained neural network model:

firstly reading whether a fat degeneration state of the rotator cuff is a normal state or an abnormal state; and when a result of the reading is that the fat degeneration state of the rotator cuff is an abnormal state, secondly reading a fat degeneration level of the rotator cuff.

11. The method of claim 10, wherein the reading of the fat degeneration level of the rotator cuff includes calculating a degree of fat degeneration based on an area of fat present in the rotator cuff, and reading the fat degeneration level based on the calculated degree of fat degeneration.

12. The method of claim 11, wherein the degree of fat degeneration is calculated based on a formula expressed as $(B-A)/B$, wherein B is an area of the rotator cuff, and A is an area excluding fat occupying the rotator cuff.

13. The method of claim 1, wherein the generating of the result information on the medical data includes generating result information including a treatment guide based on the read fat degeneration state of the rotator cuff.

* * * * *